(12) United States Patent
Allen et al.

(10) Patent No.: US 9,611,499 B2
(45) Date of Patent: *Apr. 4, 2017

(54) METHOD FOR PRODUCING SOLUBLE RECOMBINANT INTERFERON PROTEIN WITHOUT DENATURING

(71) Applicant: Pfenex Inc., San Diego, CA (US)

(72) Inventors: Jeffrey Allen, Poway, CA (US);
Ping-Hua Feng, San Diego, CA (US);
Anant Patkar, San Diego, CA (US);
Keith L. Haney, San Diego, CA (US);
Lawrence Chew, San Diego, CA (US);
Lei Lei Phokham Sengchanthalangsy, Carlsbad, CA (US)

(73) Assignee: PFENEX INC., San Diego, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/884,081

(22) Filed: Oct. 15, 2015

(65) Prior Publication Data

US 2016/0032345 A1 Feb. 4, 2016

Related U.S. Application Data

(63) Continuation of application No. 13/039,183, filed on Mar. 2, 2011, now Pat. No. 9,187,543.

(60) Provisional application No. 61/310,671, filed on Mar. 4, 2010.

(51) Int. Cl.
*C07K 14/555* (2006.01)
*A61K 38/21* (2006.01)
*C12P 21/02* (2006.01)

(52) U.S. Cl.
CPC .............. *C12P 21/02* (2013.01); *A61K 38/21* (2013.01); *C07K 14/555* (2013.01)

(58) Field of Classification Search
CPC ...... C07K 14/555; A61K 38/212; C12P 21/02
See application file for complete search history.

(56) References Cited

U.S. PATENT DOCUMENTS

| | | | |
|---|---|---|---|
| 4,462,940 A | 7/1984 | Hanisch et al. | |
| 4,551,433 A | 11/1985 | Deboer | |
| 4,588,585 A | 5/1986 | Mark et al. | |
| 4,695,455 A | 9/1987 | Barnes et al. | |
| 4,734,362 A | 3/1988 | Hung et al. | |
| 4,755,465 A | 7/1988 | Gray et al. | |
| 4,810,643 A | 3/1989 | Souza | |
| 4,861,595 A | 8/1989 | Barnes et al. | |
| 4,904,584 A | 2/1990 | Shaw | |
| 4,992,271 A | 2/1991 | Hanisch et al. | |
| 5,055,294 A | 10/1991 | Gilroy | |
| 5,128,130 A | 7/1992 | Gilroy et al. | |
| 5,169,760 A | 12/1992 | Wilcox | |
| 5,183,746 A | 2/1993 | Shaked et al. | |
| 5,240,834 A | 8/1993 | Frankel et al. | |
| 5,281,532 A | 1/1994 | Rammler et al. | |
| 5,508,192 A | 4/1996 | Georgiou et al. | |
| 5,643,566 A | 7/1997 | Hanisch et al. | |
| 5,702,699 A | 12/1997 | Hanisch et al. | |
| 5,824,778 A | 10/1998 | Ishikawa et al. | |
| 5,824,784 A | 10/1998 | Kinstler et al. | |
| 6,531,122 B1 | 3/2003 | Pedersen et al. | |
| 6,994,847 B2 | 2/2006 | Wolfe et al. | |
| 7,001,892 B1 | 2/2006 | Chmielewski et al. | |
| 7,070,989 B2 | 7/2006 | Lee et al. | |
| 7,214,367 B2 | 5/2007 | Soos et al. | |
| 7,470,675 B2 | 12/2008 | Horton et al. | |
| 7,618,799 B2 | 11/2009 | Coleman et al. | |
| 7,625,555 B2 | 12/2009 | Wang et al. | |
| 7,662,369 B2 | 2/2010 | Wolfe et al. | |
| 7,759,109 B2 | 7/2010 | Studier | |
| 7,901,670 B2 * | 3/2011 | Park .................... | C07K 14/565 424/85.6 |
| 7,985,564 B2 | 7/2011 | Retallack et al. | |
| 8,288,127 B2 | 10/2012 | Schneider et al. | |
| 8,455,218 B2 | 6/2013 | Jin et al. | |
| 8,603,824 B2 | 12/2013 | Ramseier et al. | |
| 8,940,878 B2 | 1/2015 | Shultz et al. | |
| 2003/0167531 A1 | 9/2003 | Russell et al. | |
| 2005/0283000 A1 | 12/2005 | Menart et al. | |
| 2006/0008877 A1 | 1/2006 | Retallack et al. | |
| 2006/0040352 A1 | 2/2006 | Retallack et al. | |
| 2006/0110747 A1 | 5/2006 | Ramseier et al. | |
| 2006/0234346 A1 | 10/2006 | Retallack et al. | |
| 2007/0292918 A1 | 12/2007 | Stelman et al. | |
| 2008/0193974 A1 | 8/2008 | Coleman et al. | |
| 2008/0269070 A1 | 10/2008 | Ramseier et al. | |
| 2009/0092582 A1 | 4/2009 | Bogin et al. | |
| 2009/0215121 A1 | 8/2009 | Mendiratta et al. | |
| 2009/0275518 A1 | 11/2009 | Gonthier et al. | |
| 2009/0325230 A1 | 12/2009 | Schneider et al. | |
| 2010/0137162 A1 | 6/2010 | Retallack et al. | |
| 2011/0217784 A1 | 9/2011 | Allen et al. | |
| 2011/0245474 A1 | 10/2011 | Jin et al. | |

FOREIGN PATENT DOCUMENTS

AU 7638091 A 11/1991
AU 1094892 A 8/1992
(Continued)

OTHER PUBLICATIONS

Ami et al., FT-IR study of heterologous protein expression in recombinant *Escherichia coli* strains. Biochimica et Biophysica Acta, 1624:6-10 (2003).

(Continued)

*Primary Examiner* — Robert Landsman
*Assistant Examiner* — Bruce D Hissong
(74) *Attorney, Agent, or Firm* — Wilson Sonsini Goodrich & Rosati

(57) ABSTRACT

The present invention relates to the field of recombinant protein production in bacterial hosts. It further relates to extraction of soluble, active recombinant protein from an insoluble fraction without the use of denaturation and without the need for a refolding step. In particular, the present invention relates to a production process for obtaining high levels a soluble recombinant Type 1 interferon protein from a bacterial host.

28 Claims, 9 Drawing Sheets

(56) References Cited

FOREIGN PATENT DOCUMENTS

| | | |
|---|---|---|
| EP | 0207459 A2 | 1/1987 |
| EP | 0243153 A2 | 10/1987 |
| EP | 0272703 A1 | 6/1988 |
| EP | 0331186 A2 | 9/1989 |
| EP | 0335423 A2 | 10/1989 |
| EP | 0401384 A1 | 12/1990 |
| EP | 0459630 A2 | 12/1991 |
| EP | 0473268 A2 | 3/1992 |
| EP | 1939212 A1 | 7/2008 |
| JP | H11501820 A | 2/1999 |
| RU | 2573909 C2 | 1/2016 |
| WO | WO-9012874 A2 | 11/1990 |
| WO | WO-9206116 A1 | 4/1992 |
| WO | WO-9513393 A1 | 5/1995 |
| WO | WO-9521254 A1 | 8/1995 |
| WO | WO-9533057 A1 | 12/1995 |
| WO | WO-9639422 A2 | 12/1996 |
| WO | WO-9639523 A2 | 12/1996 |
| WO | WO-9958662 A1 | 11/1999 |
| WO | WO-0049146 A1 | 8/2000 |
| WO | WO-0173081 A1 | 10/2001 |
| WO | WO-0220766 A2 | 3/2002 |
| WO | WO-0220767 A2 | 3/2002 |
| WO | WO-02066514 A2 | 8/2002 |
| WO | WO-02069232 A2 | 9/2002 |
| WO | WO-02077034 A2 | 10/2002 |
| WO | WO-03006501 A2 | 1/2003 |
| WO | WO-03023050 A2 | 3/2003 |
| WO | WO-03027288 A1 | 4/2003 |
| WO | WO-03031464 A2 | 4/2003 |
| WO | WO-03076567 A2 | 9/2003 |
| WO | WO-2004020576 A2 | 3/2004 |
| WO | WO-2005052151 A1 | 6/2005 |
| WO | WO-2005069913 A2 | 8/2005 |
| WO | WO-2005089093 A2 | 9/2005 |
| WO | WO-2006014899 A2 | 2/2006 |
| WO | WO-2007107882 A2 | 9/2007 |
| WO | WO-2008094986 A2 | 8/2008 |
| WO | WO-2008134461 A2 | 11/2008 |
| WO | WO 2011/109556 A2 | 9/2011 |

OTHER PUBLICATIONS

Ami et al., Structural analysis of protein inclusion bodies by Fourier transform infrared microspectroscopy. Biochimica et Biophysica Acta, 1764:793-799 (2006).
Australian Patent Application No. 2011223627 Examination Report dated Nov. 6, 2014.
Bongfen et al., The N-terminal domain of Plasmodium falciparum circumsporozoite protein represents a target of protective immunity, The N-terminal domain of Plasmodium falciparum circumsporozoite protein represents a target of protective immunity, Vaccine, 27(2):328-35 (2009).
Botos et al., "The Catalytic Domain of *Escherichia coli* Lon Protease Has a Unique Fold and a Ser-Lys Dyad in the Active Site," 2004, The Journal of Biological Chemistry, vol. 279, No. 9: 8140-8148.
Buchanan and Gibbons (eds.), "Gram-Negative Aerobic Rods and Cocci," Bergey's Manual of Determinative Bacteriology, pp. 217-289 (8th ed., 1974)(The Williams & Wilkins Co., Baltimore, MD, USA).
Chile Patent Application No. 2012-02378, Office Action dated Aug. 13, 2014 (with attached English language letter of explanation dated Oct. 27, 2014 from the foreign associate).
Choi et al., "Development and optimization of two-stage cyclic fed-batch culture for hG-CSF production using L-arabinose promoter of *Escherichia coli*," Bioprocess and Biosystems Engineering 24 (2001) 51-58.
Choi et al., "Plasmid Stability in Long-Term hG-CSF Production Using L-Arabinose Promoter System of *Escherichia coli*," J. Microbiol. Biotechnol. (2000) 10(3), 321-326.
Chung et al., "Overproduction of Human Granulocyte-Colony Stimulating Factor Fused to the PelB Signal Peptide in *Escherichia coli*," Journ. of Fermentation and Bioengineering, vol. 85, No. 4, 443-446 (1998).
Chinese Patent Application No. CN201180021026.9 Office Action dated Feb. 4, 2015.
Chinese Patent Application No. CN201180021026.9 Office action dated Mar. 24, 2014.
CO12-146.129 Office Action dated Jul. 8, 2014 (with attached English language letter of explanation dated Aug. 27, 2014 from the foreign associate).
CO12-146.129 Refusal Decision dated Dec. 16, 2014 (with attached English language letter of explanation dated Jan. 13, 2015 from the foreign associate).
Covalt J.C.et al., "Temperature, media, and point of induction affect the N-terminal processing of interleukin-1beta," Protein Expr Purif 41: 45-52 (2005).
Cusi M. Grazia and D. Ferrero, Harlequin granulocyte-colony stimulating factor interleukin 6 molecules with bifunctional and antagonistic activities, Immunotechnology JID-9511979 3 (1):61-69, 1997.
Davis, Bernard D., et al., Mutants of *Escherichia coli* Requiring Methionine or Vitamin B(12), J. Bact., 1950, pp. 17-28, vol. 60.
Devlin et al., "Alteration of amino-terminal codons of human granulocyte-colony-stimulating factor increases expression levels and allows efficient processing by methionine aminopeptidase in *Escherichia coli*," Gene, 65 (1988) 13-22.
EP11751317.6 Extended European Search Report dated Jan. 8, 2014.
Frishman, Dmitrij, et al., Starts of bacterial genes: estimating the reliability of computer predictions, Gene, 1999, vol. 234, Elsevier Science B.V., pp. 257-265.
Ghane, et al., "Over Expression of Biologically Active Interferon Beta Using Synthetic Gene in *E. coli*," Journ. of Sciences, Islamic Republic of Iran 19(3): 203-209 (2008).
Gilbert et al., "A New Cell Surface Proteinase: Sequencing and Analysis of the prtB Gene from *Lactobacillus delbrueckii* subsp. Bulgaricus," Journal of Bacteriology, 1996, 178(11): 3059-3065.
Hammerling et al., "In Vitro bioassay with enhanced sensitivity for human granulocyte colony-stimulating factor." J. Pharm. Biomed. Anal. 3 (1995) 9-20.
Herman et al., "Characterization, formulation and stability of Neupogen (Filgrastim), a recombinant human granulocyte-colony stimulation factor." Pharmaceutical Biotechnology, edited by Pearlman and Wang, vol. 9, (1996) 303-28.
Hong et al., "Production of biologically active hG-CSF by transgenic plant cell suspension culture," Enzyme and Microbial Technology 30 (2002) 763-767.
Ikehata, O., et al., Primary structure of nitrile hydratase deduced from the nucleotide sequence of a *Rhodococcus* species and its expression in *Escherichia coli*, 1989, Eur. J. Biochem, pp. 563-570, vol. 181.
Japan Patent Application No. 2012-556223, Office Action dated Jan. 21, 2015 (with translation).
Jeong et al., "Secretory Production of Human Granulocyte Colony-Stimulating Factor in *Escherichia coli*," Protein Expression and Purification 23, 311-318 (2001).
Jevsevar et al., "Production of Nonclassical Inclusion Bodies from Which Correctly Folded Protein Can Be Extracted," Biotechnol. P. (2005) 21, 632-639.
Jin, H., et al., "Soluble periplasmic production of human granulocyte colony-stimulating factor (G-CSF) in Pseudomonas fluorescens," 2011, Protein Expression and Purification, vol. 78, No. 1, pp. 69-77.
Kang et al., "High Level Expression and Simple Purification of Recombinant Human Granulocyte Colony-Stimulating Factor in *E. coli*," Biotechnology Letters, vol. 17, No. 7 (1995) 687-692.
Keiler, K.C. & Sauer, R.T., "Identification of Active site Residues of the Tsp Protease," The Journal of Biological Chemistry, 1995, vol. 270, No. 48, pp. 28864-28868.
Kontsek, P., "Human type I interferons: structure and function," Acta Virol. 38(6):345-60, Oritani, et al., 2001.

(56) References Cited

OTHER PUBLICATIONS

Kramer, Irene, Ph.D., "Recombinant G-CSF products and what pharmacists need to know," European Journal of Hospital Pharmacists, May 2011, vol. 17, pp. 36-45.

Krishna R. et al., (2008) Mol Biotechnology "Optimization of the AT-content of Codons Immediately Downstream of the Initiation Codon and Evaluation of Culture Conditions for High-level Expression of Recombinant Human G-CSF in *Escherichia coli*," 38:221-232.

LaFleur, et al., "Interferon-kappa, a novel type I interferon expressed in human keratinocytes," J. Biol. Chem. 276 (43), 39765-39771 (2001).

Louis et al., "Specificity of Pseudomonas aeruginosa serralysin revisited using biologically active peptides as substrates," Biochimica et Biophysica Acta, 1998, pp. 378-386.

Meager A, "Biological assays for interferons," J. Immunol. Methods 261(1-2):21-36 (Mar. 1, 2002).

NEUPOGEN (Filgrastim) Prescription Drug Product Insert (Sep. 2007).

Ohno et al. eds., Cellular engineering separate volume, Test protocol series, Protein test protocols 1: Function Analysis. Apr. 1997, Shujunsa Co., Ltd., 7 pages: p. 22, 58-61 and 232. [This article was cited in Japan Patent Application No. 2012-556223, Office Action dated Jan. 21, 2015 ].

Okabe, et al., "In vitro and in vivo hematopoietic effect of mutant human granulocyte colony-stimulating factor," Blood, 75, (1990), pp. 1788-1793.

Oritani et al., "Type I interferons and limitin: a comparison of structures, receptors, and functions," Cytokine Growth Factor Rev 12(4):337-48 (1994).

Pallen, M.J. & Wren, B.W., "The HtrA Family of serine proteases," Molecular Microbiology, 1997, 26(2), pp. 209-221.

Patterson-Ward et al., "Detection and characterization of two ATP-dependent conformational changes in proteolytically inactive *Escherichia coli* Lon mutants by stopped flow kinetic techniques," Biochemistry, 2007, 46(47): 13593-13605 doi:10.1021/bi701649b.

PCT/US2011/026921 International Search Report and Written Opinion dated Nov. 23, 2011.

PCT/US2011/026921 International Report on Patentability dated Aug. 20, 2012.

PCT/US2011/030593 International Report on Patentability dated Oct. 2, 2012.

PCT/US2011/030593 International Search Report dated Dec. 23, 2011.

Perez-Perez et al., "DNAK/DNAJ Supplementation Improves the Periplasmic Production of Human Granulocyte-Colony Stimulating Factor in *Escherichia coli*," Biochemical and Biophysical Research Communications, vol. 210, No. 2, 1995, pp. 524-529.

Peternel et al, Engineering inclusion bodies for non-denaturing extraction of functional proteins, Microbial Cell Factories, 7(34):2-3 & 6 (2008).

Retallack, et al., "Transport of heterologous proteins to the periplasmic space of Pseudomonas fluorescens using a variety of native signal sequences," Biotechnology Letters, Springer Netherlands, Dordrecht, vol. 29, No. 10, May 31, 2007, pp. 1483-1491.

Riesenberg, D et al., 1991, "High cell density cultivation of *Escherichia coli* at controlled specific growth rate," J. Biotechnol. 20 (1):17-27.

Russian Patent Application No. 2012141653 Office Action dated Nov. 15, 2014.

Russell-Harde, 1995, The Use of Zwittergent 3-14 in the Purification of Recombinant Human Interferon-β Ser17 (Betaseron) et al., J. Interferon and Cytokine Res. 15:31-37.

Sakoh et al., "Proteolytic Activity of HtpX, a Membrane-bound and Stress-controlled Protease from *Escherichia coli*," 2005, Journal of Biological Chemistry, vol. 280, No. 39, pp. 33305-33310.

Sanchez-Romero, Genetic Engineering of Nonpathogenic Pseudomonas strains as Biocatalysts for Industrial and Environmental Processes, Manual of Industrial Microbiology and Biotechnology, Demain and Davies, eds., pp. 460-474 (ASM Press, Washington DC) 1999.

Schneider et al., (2005) "Auxotrophic markers pyrF and proC can replace antibiotic markers on protein production plasmids in high-cell-density Pseudomonas fluorescens fermentation," 2005a, Biotechnology Progress 21(2): 343-348.

Schrodel et al., "Characterization of the aggregates formed during recombinant protein expression in bacteria," BMC Biochemistry 2005, 6:10.

Schweizer, Herbert P., Vectors to Express Foreign Genes and Techniques to Monitor Gene Expression in Pseudomonads, Current Opinion in Biotechnology, 2001, vol. 12, Elsevier Science Ltd., pp. 439-445.

Slater, Robert J., and Williams,Ross, "The Expression of Foreign DNA in Bacteria," 2000, Molecular Biology and Biotechnology, Fourth Edition, Chapter 4, The Royal Society of Chemistry, Cambridge, UK, pp. 125-154.

Sorg, J. Enczmann, U. Sorg, K. Heermeier, E. M. Schneider, and P. Wernet. Rapid and sensitive mRNA phenotyping for interleukins (IL-1 to IL-6) and colony-stimulating factors (G-CSF, M-CSF, and GM-CSF) by reverse transcription and subsequent polymerase chain reaction, Exp Hematol JID-0402313 19 (9):882-887, 1991.

Squires, et al., "Heterologous protein production in P. Fluorescens," Bioprocess International, 2004, vol. 2, No. 11, pp. 54-59.

Suzek, Baris E., et al., "A Probabilistic Method for Identifying Start Codons in Bacterial Genomes." Bioinformatics, 2001, pp. 1123-1130, vol. 17, No. 12, Oxford University Press.

Tanaka et al., "Three types of recombinant human granulocyte colony-stimulating factor have equivalent biological activities in monkeys," Cytokine 9, (1997), pp. 360-369.

U.S. Appl. No. 13/039,183 Office Action dated May 1, 2014.
U.S. Appl. No. 13/039,183 Office Action dated Nov. 28, 2014.
U.S. Appl. No. 13/039,183 Office Action dated Sep. 6, 2013.
U.S. Appl. No. 13/076,315 Office Action dated Jun. 4, 2012.
U.S. Appl. No. 13/076,315 Office Action dated Oct. 10, 2012.

Valente, et al., 2004, "Translational Features of Human Alpha 2b Interferon Production in *Escherichia coli*," Applied and Environmental Microbiology 70(8): 5033-5036.

Vanz et al., "Human Granulocyte Colony Stimulating factor (hG-CSF): cloning, overexpression, purification and characterization," Microbial Cell Factories 2008, 7:13.

Welch et al., PLoS One, Design Parameters to Control Synthetic Gene Expression in *Escherichia coli*, 4(9):e7002 (10 pgs) (2009).

Weston, B., Todd, R. F., 3rd, Axtell, R., Balazovich, K., Stewart, J., Locey, B. J., Mayo-Bond, L., Loos, P., Hutchinson, R. & Boxer, L. A. (1991). Severe congenital neutropenia: clinical effects and neutrophil function during treatment with granulocyte colony-stimulating factor. J Lab Clin Med 117, 282-90.

Wingfield et al., "Characterization of recombinant-derived granulocyte-colony stimulating factor (G-CSF)," Biochem. J. (1988) 256, 213-218.

Yoon et al., "Secretory Production of Recombinant Proteins in *Escherichia coli*," Recent Patents on Biotechnology, 4, 23-29 (2010).

Zaveckas et al., "Effect of Surface histidine mutations and their number on the partitioning and refolding of recombinant human granulocyte-colony stimulating factor (Cys17Ser) in aqueous two-phase systems containing chelated metal ions," Journ. of Chromatography B, 852 (2007) 409-419.

Mexican Patent Application No. MX/a/2012/010148 Second Office Action dated Jan. 20, 2016 (in Spanish) and foreign associate's reporting letter (in English).

\* cited by examiner

A

| Term | Estimate | Std Error | t Ratio | | Prob>\|t\| |
|---|---|---|---|---|---|
| Z314 | 3720.4167 | 489.4339 | 7.60 | | <.0001* |
| Solids | -92.575 | 29.36603 | -3.15 | | 0.0103* |
| Urea | 615.9375 | 220.2452 | 2.80 | | 0.0189* |
| (Solids-12.5)*(Z314-0.55) | -127.5 | 65.25785 | -1.95 | | 0.0792 |
| NaCl | 500.51471 | 259.112 | 1.93 | | 0.0822 |
| (NaCl-1)*(Z314-0.55) | 1008.3333 | 575.8046 | 1.75 | | 0.1105 |
| pH | 353.1875 | 220.2452 | 1.60 | | 0.1399 |
| (Solids-12.5)*(NaCl-1) | -30.7549 | 34.54827 | -0.89 | | 0.3943 |

MSYNLLGFLQRSSNFQSQKLLWQLNGRLEYCLKDRMNFDIPEEIKQLQQFQKED
AALTIYEMLQNIFAIFRQDSSSTGWNETIVENLLANVYHQINHLKTVLEEKLEKED
FTRGKLMSSLHLKRYYGRILHYLKAKEYSHCAWTIVRVEILRNFYFINRLTGYLR
N (SEQ ID NO: 1)

B

Atgtcgtacaacctgttgggcttcctgcagcggtcctccaactttcaatcgcagaagctgctgtggcaattgaatggtcgcctgga
atactgcctgaaggaccgcatgaacttcgacatccctgaagagattaagcaactccagcagttccagaaagaggatgcagctct
gacgatctatgaaatgctgcagaacatcttcgcgatctttcgccaggacagcagcagcaccggttggaacgaaaccattgtcga
gaatctgctggccaacgtctatcaccagattaaccacctcaagactgtgctggaagagaagttggagaaagaagatttcacgcgt
ggcaagttgatgagttcgctgcatttgaaacgctactatggtcgtatcctgcattacctgaaggccaaagaatacagccactgtgc
gtggaccatcgttcgcgtggagatcctgcgcaacttctacttcatcaatcggctcaccggttacctccgcaact (SEQ ID
NO: 2)

C

SYNLLGFLQRSSNFQSQKLLWQLNGRLEYCLKDRMNFDIPEEIKQLQQFQKEDA
ALTIYEMLQNIFAIFRQDSSSTGWNETIVENLLANVYHQINHLKTVLEEKLEKEDF
TRGKLMSSLHLKRYYGRILHYLKAKEYSHCAWTIVRVEILRNFYFINRLTGYLRN
(SEQ ID NO: 3)

```
  1  C  D  L  P  Q  T  H  S  L  G  S  R  R  T  L  M  L  L  A  Q
 21  M  R  K  I  S  L  F  S  C  L  K  D  R  H  D  F  G  F  P  Q
 41  E  E  F  G  N  Q  F  Q  K  A  E  T  I  P  V  L  H  E  M  I
 61  Q  Q  I  F  N  L  F  S  T  K  D  S  S  A  A  W  D  E  T  L
 81  L  D  K  F  Y  T  E  L  Y  Q  Q  L  N  D  L  E  A  C  V  I
101  Q  G  V  G  V  T  E  T  P  L  M  K  E  D  S  I  L  A  V  R
121  K  Y  F  Q  R  I  T  L  Y  L  K  E  K  K  Y  S  P  C  A  W
141  E  V  V  R  A  E  I  M  R  S  F  S  L  S  T  N  L  Q  E  S
161  L  R  S  K  E   (SEQ ID NO: 4)
```

B

```
  1  TGTGACCTGCCTCAGACTCACTCCCTCGGTAGCCGCCGGACCCTGATGCTGTTGGCGCAG
 61  ATGCGTAAGATCTCCCTGTTCTCGTGCCTGAAAGACCGCCATGATTTCGGCTTCCCGCAG
121  GAAGAATTCGGGAACCAGTTTCAGAAGGCTGAAACCATCCCAGTGCTGCACGAGATGATC
181  CAGCAAATTTTCAACCTGTTCAGCACCAAGGACAGCTCGGCCGCCTGGGACGAAACGTTG
241  TTGGACAAATTTTACACCGAGCTGTACCAACAACTGAACGATCTGGAAGCATGCGTTATT
301  CAAGGCGTGGGCGTCACCGAAACGCCGCTGATGAAAGAAGATAGCATCCTGGCCGTGCGT
361  AAGTACTTTCAGCGCATCACCCTCTACCTGAAAGAGAAGAAGTATTCGCCCTGCGCGTGG
421  GAGGTCGTCCGCGCCGAGATCATGCGGTCCTTCAGCCTCTCCACCAATCTGCAGGAAAGT
481  CTCCGCTCGAAAGAA   (SEQ ID NO: 5)
```

```
  1  C  D  L  P  Q  T  H  S  L  G  S  R  R  T  L  M  L  L  A  Q
 21  M  R  R  I  S  L  F  S  C  L  K  D  R  H  D  F  G  F  P  Q
 41  E  E  F  G  N  Q  F  Q  K  A  E  T  I  P  V  L  H  E  M  I
 61  Q  Q  I  F  N  L  F  S  T  K  D  S  S  A  A  W  D  E  T  L
 81  L  D  K  F  Y  T  E  L  Y  Q  Q  L  N  D  L  E  A  C  V  I
101  Q  G  V  G  V  T  E  T  P  L  M  K  E  D  S  I  L  A  V  R
121  K  Y  F  Q  R  I  T  L  Y  L  K  E  K  K  Y  S  P  C  A  W
141  E  V  V  R  A  E  I  M  R  S  F  S  L  S  T  N  L  Q  E  S
161  L  R  S  K  E     (SEQ ID NO: 6)
```

B

```
  1  TGTGACCTGCCTCAGACTCACTCCCTCGGTAGCCGCCGGACCCTGATGCTGTTGGCGCAG
 61  ATGCGTCGCATCTCCCTGTTCTCGTGCCTGAAAGACCGCCATGATTTCGGCTTCCCGCAG
121  GAAGAATTCGGGAACCAGTTTCAGAAGGCTGAAACCATCCCAGTGCTGCACGAGATGATC
181  CAGCAAATTTTCAACCTGTTCAGCACCAAGGACAGCTCGGCCGCCTGGGACGAAACGTTG
241  TTGGACAAATTTTACACCGAGCTGTACCAACAACTGAACGATCTGGAAGCATGCGTTATT
301  CAAGGCGTGGGCGTCACCGAAACGCCGCTGATGAAAGAAGATAGCATCCTGGCCGTGCGT
361  AAGTACTTTCAGCGCATCACCCTCTACCTGAAAGAGAAGAAGTATTCGCCCTGCGCGTGG
421  GAGGTCGTCCGCGCCGAGATCATGCGGTCCTTCAGCCTCTCCACCAATCTGCAGGAAAGT
481  CTCCGCTCGAAAGAA    (SEQ ID NO: 7)
```

METHOD FOR PRODUCING SOLUBLE RECOMBINANT INTERFERON PROTEIN WITHOUT DENATURING

CLAIM OF PRIORITY

The application is a Continuation of U.S. application Ser. No. 13/039,183, filed Mar. 2, 2011, which claims the benefit of Provisional Application No. 61/310,671, filed Mar. 4, 2010, the contents of which are herein incorporated by reference in their entirety.

SEQUENCE LISTING

The instant application contains a Sequence Listing which has been submitted in ASCII format via EFS-Web and is hereby incorporated by reference in its entirety. Said ASCII copy, created on Feb. 11, 2011, is named 38194201.txt and is 9,237 bytes in size.

BACKGROUND OF THE INVENTION

Many heterologous recombinant proteins are produced in a misfolded insoluble form, called inclusion bodies, when expressed in bacterial systems. In general, denaturing reagents must be used to solubilize the recombinant protein in the inclusion bodies. The protein must then be renatured, under conditions that have been optimized for the protein to properly fold. Efforts expended on optimization, as well as the slow refolding process and lowered process yields, add cost and time to the production of a recombinant protein.

Interferons exhibit antiviral, antiproliferative, immunomodulatory, and other activities. Several distinct types of human interferons, including α, β, and γ, have been distinguished based on, e.g., their anti-viral and anti-proliferative activities. Interferon secretion is induced by signals, including viruses, double-stranded RNAs, other polynucleotides, antigens, and mitogens. Interferon-β is an example of a protein that has been expressed in recombinant form in bacteria, where it is sequestered in inclusion bodies.

Human interferon-β 1b is a regulatory polypeptide having a molecular weight of about 22 kDa and consisting of 165 amino acid residues. It can be produced by many cells in the body, in particular fibroblasts, in response to viral infection or exposure to other biologics. It binds to a multimeric cell surface receptor. Productive receptor binding results in a cascade of intracellular events leading to the expression of interferon-β inducible genes and triggering antiviral, antiproliferative and immunomodulatory activity.

Interferon-β 1b, specifically, Betaseron (h-IFN-β 1b C17S), has been used to treat diseases including multiple sclerosis (MS), hepatitis B and C infections, glioma, and melanoma. Interferon-β has been demonstrated to reduce the number of attacks suffered by patients with relapsing and remitting MS. Substantial amounts of interferon-β 1b are needed for therapeutic use. Recombinant interferon-β 1b has been produced at low levels in mammalian cells, including human fibroblasts and CHO cells. Animal cell expression is typically hindered by technical difficulties including longer process time, easy contamination of cultures, a requirement for maintaining stringent culturing conditions, and the high cost of culture media. As the glycoprotein component has been found to be generally unnecessary for the activity of interferon β, research has turned to the expression of the recombinant protein in the bacterial expression system, *E. coli*. As noted, the inclusion bodies generated in *E. coli* must be solubilized by denaturation, and the interferon-β refolded. Refolding, which is slow, extends process time, adds cost, and lowers yield. To date, a method for quickly and economically producing high levels of soluble recombinant interferon-β in either mammalian or bacterial host cells, without the need for denaturing and refolding steps, has not been described.

SUMMARY OF THE INVENTION

The present invention relates to the expression of interferon in *P. fluorescens* and development of a new method to extract active proteins from the fermentation product using mild detergents and without the need for a refolding process.

In particular, the present invention provides a method for producing a recombinant Type 1 interferon protein, said method comprising expressing the recombinant interferon protein by culturing a *Pseudomonas* or *E. coli* host cell containing an expression construct comprising a coding sequence that has been optimized for expression in the host cell, lysing the host cell, obtaining an insoluble fraction and a soluble fraction from the lysis step, extracting the insoluble fraction by subjecting it to non-denaturing extraction conditions, and obtaining an extract pellet and an extract supernatant from the insoluble fraction, wherein the recombinant protein in the extract supernatant is present in soluble form, active form, or a combination thereof, without being further subjected to a renaturing or refolding step.

In embodiments, the non-denaturing extraction conditions comprise the presence of a mild detergent. In certain embodiments, the mild detergent is a Zwitterionic detergent. In specific embodiments, the Zwitterionic detergent is Zwittergent 3-08, Zwittergent 3-10, Zwittergent 3-12, or Zwittergent 3-14. In embodiments, the non-denaturing extraction conditions comprise about 0.5% to about 2% Zwittergent 3-14. In certain embodiments, the mild detergent is not N-lauroyl-sarcosine (NLS).

In embodiments, the non-denaturing extraction conditions comprise the presence of a mild detergent and further comprise a chaotropic agent and a cosmotropic salt. In certain embodiments, the chaotropic agent is urea or guanidinium hydrochloride, and the cosmotropic salt is NaCl, KCl, or $(NH_4)_2SO_4$. In specific embodiments, the non-denaturing extraction conditions comprise about 0.5 to about 2% Zwittergent 3-14; about 0 to about 2 M urea; about 0 to about 2 M NaCl; and the pH is about 6.5 to about 8.5. In embodiments, the non-denaturing extraction conditions comprise: 1% Zwittergent 3-14; 2 M urea; 2 M NaCl; and the pH is about 8.2. In other embodiments, the non-denaturing extraction conditions additionally comprise about 1% to about 40% w/v solids. In certain embodiments, the non-denaturing extraction conditions additionally comprise about 5% w/v solids.

In embodiments, the recombinant Type 1 interferon protein is an interferon-β, an interferon-α, an interferon-κ, an interferon-τ, or an interferon-ω. In specific embodiments, the recombinant Type 1 interferon protein is an interferon-β or an interferon-α. In embodiments, the recombinant Type 1 interferon protein is an interferon-β, and said interferon-β is selected from the group consisting of: a human interferon-β 1b and human interferon-β 1b C17S. In embodiments, wherein the recombinant Type 1 interferon is an interferon-α, the interferon-α is selected from the group consisting of: human interferon-α 2a and human interferon-α 2b.

In further embodiments the claimed method further comprises measuring the amount of recombinant Type 1 interferon protein in the insoluble fraction and the extract supernatant fractions, wherein the amount of recombinant interferon protein detected in the extract supernatant fraction is about 10% to about 95% of the amount of the recombinant interferon protein detected in the insoluble fraction. In other embodiments, the method further comprises measuring the activity of the recombinant protein, wherein about 40% to about 100% of the recombinant protein present in the extract supernatant is determined to be active. In related embodiments, the recombinant protein is an interferon-β, and the amount of active recombinant protein is determined by Blue Sepharose affinity column chromatography, receptor binding assay, antiviral activity assay, or cytopathic effect assay. In other embodiments, the recombinant protein is an interferon-α, an interferon-κ, or an interferon-ω, and the amount of active recombinant protein is determined by Blue Sepharose affinity column chromatography, receptor binding assay, antiviral activity assay, or cytopathic effect assay.

The invention further includes methods for producing a recombinant Type 1 interferon protein, said method comprising expressing the recombinant interferon protein by culturing a *Pseudomonas* or *E. coli* host cell containing an expression construct comprising a coding sequence that has been optimized for expression in the host cell, lysing the host cell, obtaining an insoluble fraction and a soluble fraction from the lysis step, extracting the insoluble fraction by subjecting it to non-denaturing extraction conditions, and obtaining an extract pellet and an extract supernatant from the insoluble fraction, wherein the recombinant protein in the extract supernatant is present in soluble form, active form, or a combination thereof, without being further subjected to a renaturing or refolding step, wherein the recombinant protein is an interferon-β, and further wherein the non-denaturing extraction conditions are optimized using the information in FIG. 4B.

In embodiments, the recombinant protein in the extract supernatant is present at a concentration of about 0.3 grams per liter to about 10 grams per liter. In other embodiments, the host cell is cultured in a volume of about 1 to about 20 or more liters. In specific embodiments, the host cell is cultured in a volume of about 1 liter, about 2 liters, about 3 liters, about 4 liters, about 5 liters, about 10 liters, about 15 liters, or about 20 liters.

In embodiments of the invention, the expression construct comprises an inducible promoter. In specific embodiments, the expression construct comprises a lac promoter derivative and expression of the interferon is induced by IPTG.

In embodiments, the host cell is grown at a temperature of about 25° C. to about 33° C., at a pH of about 5.7 to about 6.5, and the IPTG is added to a final concentration of about 0.08 mM to about 0.4 mM, when the OD575 has reached about 80 to about 160. In specific embodiments, the host cell is grown at a temperature of about 32° C., at a pH of about 5.7 to 6.25, and the IPTG is added to a final concentration of about 0.2 mM, when the OD575 has reached about 120 to about 160.

In embodiments of the invention, the expression construct comprises a high activity ribosome binding site. In certain embodiments, the host cell is a lon hslUV protease deletion strain. In other embodiments, the Type 1 interferon is expressed in the cytoplasm of the host cell. In related embodiments, the Type 1 interferon is human interferon-β 1b or human interferon-β 1b C17S, and is expressed in the cytoplasm of the host cell.

The invention also provides methods for extracting a recombinant Type 1 interferon protein, wherein the recombinant interferon protein is present in an insoluble fraction, said insoluble fraction produced after lysis of a *Pseudomonas* or *E. coli* host cell expressing the recombinant interferon protein, said method comprising subjecting the insoluble fraction to non-denaturing extraction conditions, and obtaining an extract pellet from the insoluble fraction, said extract pellet comprising recombinant interferon protein, wherein the recombinant interferon protein in the extract pellet is in soluble form, active form, or a combination thereof, without being subjected to a renaturing or refolding step.

In embodiments, the recombinant Type 1 interferon protein extracted is an interferon-β, an interferon-α, an interferon-κ, an interferon-τ, or an interferon-ω. In certain embodiments, the recombinant Type 1 interferon protein is an interferon-β or an interferon-α. In embodiments, the recombinant Type 1 interferon protein is an interferon-β, and said interferon-β is selected from the group consisting of: a human interferon-β 1b and human interferon-β 1b C17S. In other embodiments, the interferon-α is selected from the group consisting of: human interferon-α 2a and human interferon-α 2b.

The invention additionally provides a method for producing an insoluble fraction comprising a recombinant Type 1 interferon protein, wherein the recombinant interferon protein is expressed in a *Pseudomonas* or *E. coli* host cell from a nucleic acid construct comprising a nucleic acid sequence that is operably linked to a lac derivative promoter, said method comprising growing the host cell at a temperature of about 25° C. to about 33° C. and at a pH of about 5.7 to about 6.5, to an OD600 of about 80 to about 160, and inducing the host cell at a concentration of about 0.08 mM to about 0.4 mM IPTG, lysing the host cell and centrifuging it to produce the pellet fraction, wherein soluble, active, or soluble and active recombinant interferon protein can be obtained by extracting the pellet fraction under non-denaturing conditions without a subsequent renaturing or refolding step.

In embodiments, the recombinant Type 1 interferon protein comprised by the insoluble fraction is an interferon-β, an interferon-α, an interferon-κ, or an interferon-ω. In specific embodiments, the recombinant Type 1 interferon protein is an interferon-β or an interferon-α. In embodiments, wherein recombinant Type 1 interferon protein is an interferon-β, the interferon-β is selected from the group consisting of: a human interferon-β 1b and human interferon-β 1b C17S. In embodiments, wherein the Type 1 interferon protein is an interferon-α, the interferon-α is selected from the group consisting of: human interferon-α 2a and human interferon-α 2b. In embodiments, in the method for producing an insoluble fraction comprising a recombinant Type 1 interferon protein, the temperature at which the host cell is grown is about 32° C., and the IPTG concentration is about 0.2 mM.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and in the accompanying drawings.

For both 1A and 1B:

Lane 1. Molecular weight ladder with sizes as indicated.

Lane 2. Pellet from initial centrifugation after cell lysis (insoluble fraction).

Lanes 3-9. Supernatant from centrifugation following extraction step. Lanes 3 to 7 represent extraction with PBS buffer, without and with 1% Zwittergent 3-14, as indicated, and Lanes 8 and 9 represent extraction with acetate buffer, without and with 1% Zwittergent 3-14, respectively.

Lanes 10-13. Pellet from spin following extraction step. Lanes 10 and 11 represent extraction with PBS buffer, without and with 1% Zwittergent 3-14, respectively, and Lanes 12 and 13 represent extraction with acetate buffer, without and with 1% Zwittergent 3-14, respectively.

Figure 2:
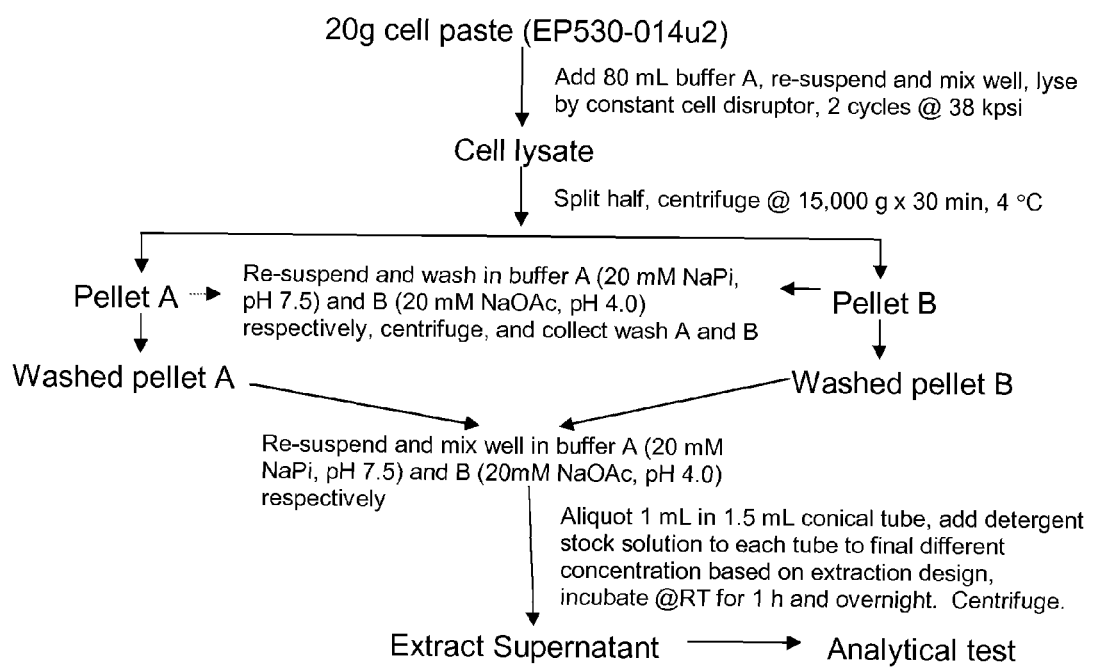

FIG. 2. Flowchart of study performed to evaluate extraction of interferon-β using different detergents.

Figure 3:
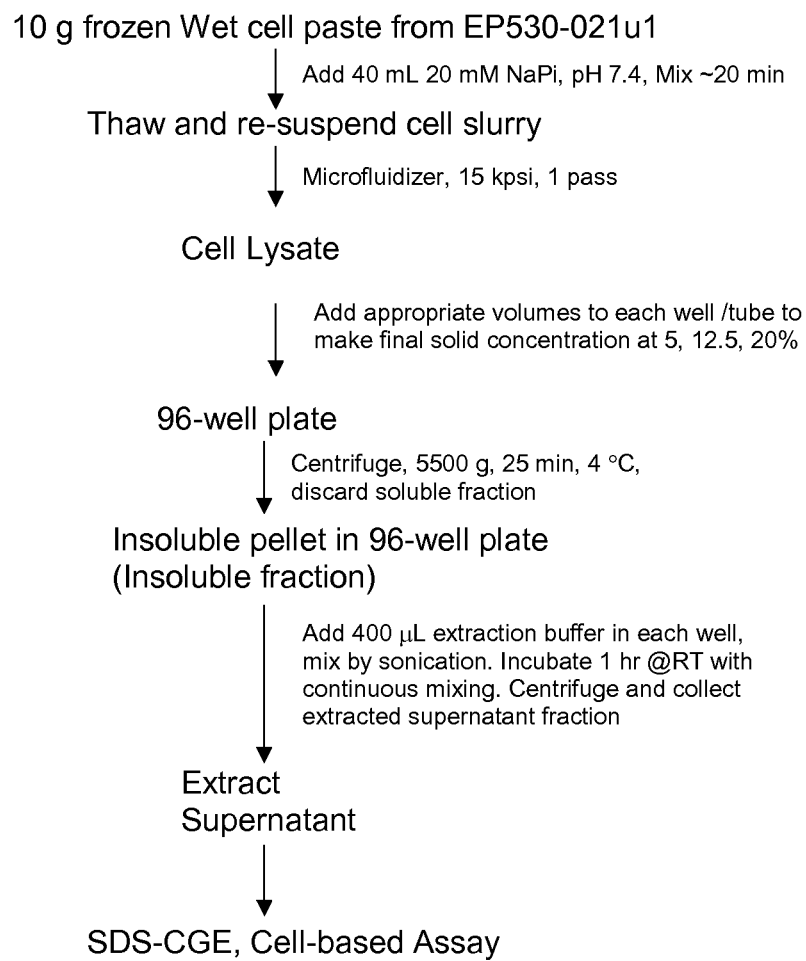

FIG. 3. Flowchart of statistically designed study performed to evaluate extraction of interferon-β using different extraction conditions including Zwittergent 3-14.

Figure 4:
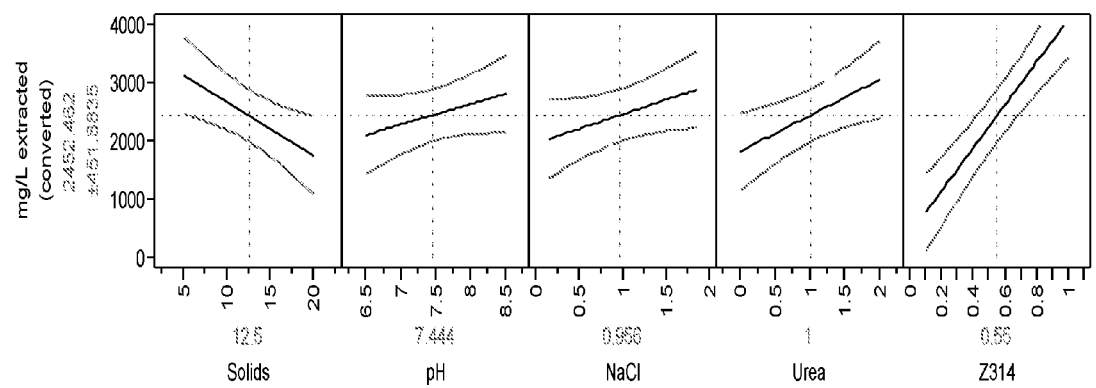

FIG. 4. Results of study performed to evaluate extraction of interferon-β using different extraction conditions including Zwittergent 3-14. A. Statistical summary. B. Ranges of useful extraction conditions.

Figure 5:
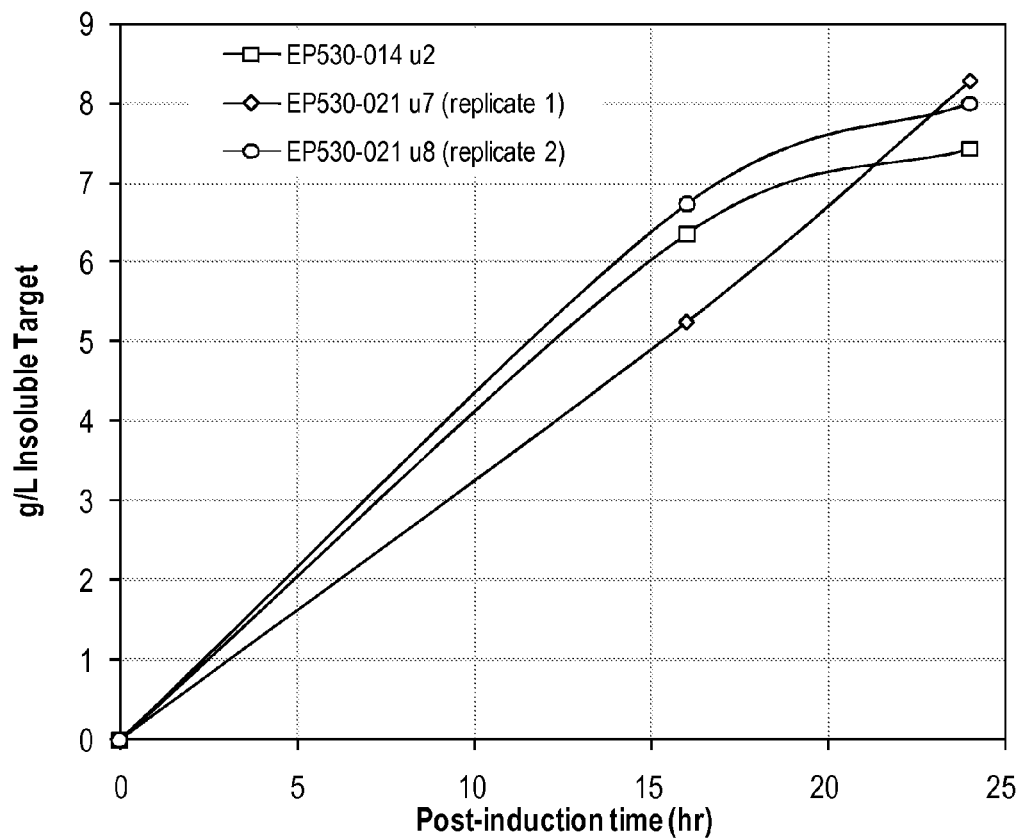

FIG. 5. Insoluble IFN-β Production over Post-Induction Time for Replicate Fermentations.

The results from three different replicates were plotted.

Figure 6:
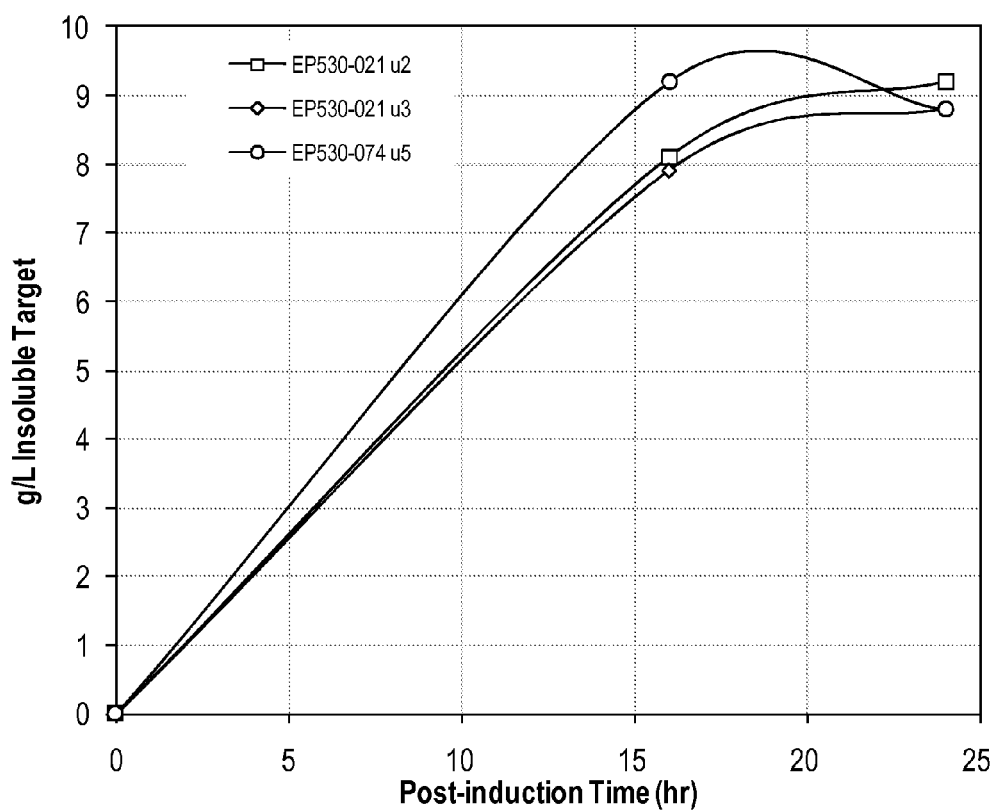

FIG. 6. Insoluble IFN-β Production over Post-Induction Time for Alternate pH and OD.

The results from three different replicates were plotted.

FIG. 7. IFN-β 1b Sequence A. IFN-β 1b C17S Amino Acid Sequence. (SEQ ID NO: 1) The sequence shows the N-terminal methionine, which is not present in the purified protein. B. IFN-β DNA Sequence with Codons Optimized for *P. fluorescens*. This sequence encodes the amino acid sequence shown in FIG. 7A. (SEQ ID NO: 2) C. IFN-β 1b C17S Amino Acid Sequence, without N-terminal methionine. (SEQ ID NO: 3)

FIG. 8. IFN-α 2a Sequence. A. IFN-α 2a Amino Acid Sequence. (SEQ ID NO: 4) B. IFN-α 2a DNA Sequence with Codons Optimized for *P. fluorescens*. (SEQ ID NO: 5)

FIG. 9. IFN-α 2b Sequence. A. IFN-α 2b Amino Acid Sequence. (SEQ ID NO: 6) B. IFN-α 2b DNA Sequence with Codons Optimized for *P. fluorescens*. (SEQ ID NO: 7)

DETAILED DESCRIPTION OF THE INVENTION

The present invention relates to a method for producing large amounts of soluble recombinant interferon protein in a *Pseudomonas* expression system. In particular, this method eliminates the need for the denaturing step and subsequent renaturing/refolding step typically required.

Production of recombinant interferon-β in bacterial expression systems has been hampered by sequestration of the protein in insoluble inclusion bodies. Solubilization of the inclusion bodies requires denaturation, which in turn necessitates the use of a refolding step that is costly, time-consuming, and decreases protein yield. The present invention circumvents the need for a refolding step by providing methods for producing and solubilizing interferon without recourse to denaturation.

Methods for producing a recombinant interferon protein that is soluble, active, or both, in a bacterial expression system, without subjecting the protein to a denaturing step, are provided. In particular, a non-denaturing extraction process that results in soluble interferon protein is described. Interferons expressed in bacterial expression systems are generally localized to an insoluble fraction. In the extraction process of the present invention, this insoluble fraction is subjected to extraction conditions that include non-denaturing concentrations of mild detergents and produce soluble protein.

Also provided by the present invention are methods for producing a recombinant interferon protein wherein growth conditions for the *Pseudomonas* host cell are optimized to maximize yields of the soluble recombinant interferon protein, particularly when the extraction method of the invention is used. Studies of the effect of *E. coli* growth conditions on soluble protein production have been reported. The solubility of a given protein when expressed in *Pseudomonas* can be different from that in *E. coli*. This is illustrated in, e.g., U.S. Pat. App. Pub. No. 2006/0040352, "Expression of Mammalian Proteins in *Pseudomonas Fluorescens*," which shows side-by-side comparisons of the soluble amounts of several proteins produced using *E. coli* or *P. fluorescens* as the host. Furthermore, there is substantial variation among the solubilities of different proteins even in the same host, as solubility is influenced strongly by protein structure, e.g., amino acid sequence. Previously reported attempts at producing IFN-β in *E. coli* resulted in protein that required refolding. See, e.g., Russell-Harde, 1995, "The Use of Zwittergent 3-14 in the Purification of Recombinant Human Interferon-β Ser17 (Betaseron) et al., J. Interferon and Cytokine Res. 15:31-37, and Ghane, et al., 2008, "Over Expression of Biologically Active Interferon Beta Using Synthetic Gene in *E. coli*," J. of Sciences, Islamic Republic of Iran 19(3):203-209, both incorporated herein by reference.

The methods further provide optimized growth conditions including growth temperature, OD at time of promoter induction, inducer concentration, and pH. Extraction conditions provided include detergent type and concentration, chaotropic agent, cosmotropic salt, and pH. Specific values as well as optimal parameter ranges are provided. Also provided are methods for optimizing extraction conditions using the provided ranges.

Bacterial Growth Conditions

In embodiments of the present invention, the bacterial growth conditions are optimized to increase the amount of soluble interferon protein obtained using the extraction methods as provided herein. Use of the growth conditions of the present invention with other extraction conditions, e.g., other methods described and used in the art, is also contemplated.

Optimal growth conditions particularly useful in conjunction with the extraction methods of the invention comprise: a temperature of about 25° C. to about 33° C.; a pH of about 5.7 to about 6.5, and induction with about 0.08 mM to about 0.4 mM IPTG when the culture has reached an $OD_{575}$ of about 80 to about 160.

The pH of the culture can be maintained using pH buffers and methods known to those of skill in the art. Control of pH during culturing also can be achieved using aqueous ammonia. In embodiments, the pH of the culture is about 5.7 to about 6.5. In certain embodiments, the pH is 5.7, 5.8, 5.9, 6.0, 6.1, 6.2, 6.3, 6.4. or 6.5. In other embodiments, the pH is 5.7 to 5.9, 5.8 to 6.0, 5.9 to 6.1, 6.0 to 6.2, 6.1 to 6.3, or 6.2 to 6.5. In yet other embodiments, the pH is 5.7 to 6.0, 5.8 to 6.1, 5.9 to 6.2, 6.0 to 6.3, 6.1 to 6.4, or 6.2 to 6.5. In certain embodiments, the pH is about 5.7 to about 6.25.

In embodiments, the growth temperature is maintained at about 25° C. to about 33° C. In certain embodiments, the growth temperature is about 25° C., about 26° C., about 27° C., about 28° C., about 29° C., about 30° C., about 31° C., about 32° C., or about 33° C. In other embodiments, the growth temperature is maintained at about 25° C. to about 27° C., about 25° C. to about 28° C., about 25° C. to about 29° C., about 25° C. to about 30° C., about 25° C. to about 31° C., about 25° C. to about 32° C., about 25° C. to about 33° C., about 26° C. to about 28° C., about 26° C. to about 29° C., about 26° C. to about 30° C., about 26° C. to about 31° C., about 26° C. to about 32° C., about 27° C. to about 29° C., about 27° C. to about 30° C., about 27° C. to about 31° C., about 27° C. to about 32° C., about 26° C. to about 33° C., about 28° C. to about 30° C., about 28° C. to about 31° C., about 28° C. to about 32° C., about 29° C. to about 31° C., about 29° C. to about 32° C., about 29° C. to about 33° C., about 30° C. to about 32° C., about 30° C. to about 33° C., about 31° C. to about 33° C., about 31° C. to about 32° C., about 30° C. to about 33° C., or about 32° C. to about 33° C.

Induction

As described elsewhere herein, inducible promoters can be used in the expression construct to control expression of the recombinant interferon gene. In the case of the lac promoter derivatives or family members, e.g., the tac promoter, the effector compound is an inducer, such as a gratuitous inducer like IPTG (isopropyl-β-D-1-thiogalactopyranoside, also called "isopropylthiogalactoside"). In embodiments, a lac promoter derivative is used, and interferon expression is induced by the addition of IPTG to a final concentration of about 0.08 mM to about 0.4 mM, when the cell density has reached a level identified by an $OD_{575}$ of about 80 to about 160.

In embodiments, the $OD_{575}$ at the time of culture induction about 80, about 90, about 100, about 110, about 120, about 130, about 140, about 150, about 160, about 170 or about 180. In other embodiments, the $OD_{575}$ is about 80 to about 100, about 100 to about 120, about 120 to about 140, about 140 to about 160. In other embodiments, the $OD_{575}$ is about 80 to about 120, about 100 to about 140, or about 120 to about 160. In other embodiments, the $OD_{575}$ is about 80 to about 140, or about 100 to about 160. The cell density can be measured by other methods and expressed in other units, e.g., in cells per unit volume. For example, an $OD_{575}$ of about 80 to about 160 of a Pseudomonas fluorescens culture is equivalent to approximately $8 \times 10^{10}$ to about $1.6 \times 10^{11}$ colony forming units per mL or 35 to 70 g/L dry cell weight. In embodiments, the cell density at the time of culture induction is equivalent to the cell density as specified herein by the absorbance at $OD_{575}$, regardless of the method used for determining cell density or the units of measurement. One of skill in the art will know how to make the appropriate conversion for any cell culture.

In embodiments, the final IPTG concentration of the culture is about 0.08 mM, about 0.1 mM, about 0.2 mM, about 0.3 mM, or about 0.4 mM. In other embodiments, the final IPTG concentration of the culture is about 0.08 mM to about 0.1 mM, about 0.1 mM to about 0.2 mM, about 0.2 mM to about 0.3 mM, about 0.3 mM to about 0.4 mM, about 0.2 mM to about 0.4 mM, or about 0.08 to about 0.2 mM.

In embodiments, the interferon is expressed by induction of a lac promoter or derivative using IPTG, lactose or allolactose, by methods known in the art and described in the literature, e.g., in U.S. Pat. No. 7,759,109, "High density growth of T7 expression strains with auto-induction option," incorporated herein by reference in its entirety.

In embodiments wherein a non-lac type promoter is used, as described herein and in the literature, other inducers or effectors can be used.

After induction is started, cultures are grown for a period of time, typically about 24 hours, during which time the recombinant interferon protein is expressed. Cell cultures can be concentrated by centrifugation, and the culture pellet resuspended in a buffer or solution appropriate for the subsequent lysis procedure.

In embodiments, cells are disrupted using equipment for high pressure mechanical cell disruption (which are available commercially, e.g., Microfluidics Microfluidizer, Constant Cell Disruptor, Niro-Soavi homogenizer or APV-Gaulin homogenizer). Any appropriate method known in the art for lysing cells can be used to release the insoluble fraction. For example, in embodiments, chemical and/or enzymatic cell lysis reagents, such as cell-wall lytic enzyme and EDTA, can be used. Use of frozen or previously stored cultures is also contemplated in the methods of the invention. Cultures can be OD-normalized prior to lysis.

Centrifugation is performed using any appropriate equipment and method. Centrifugation of cell culture or lysate for the purposes of separating a soluble fraction from an insoluble fraction is well-known in the art. For example, lysed cells can be centrifuged at 20,800×g for 20 minutes (at 4° C.), and the supernatants removed using manual or automated liquid handling. The pellet (insoluble) fraction is resuspended in a buffered solution, e.g., phosphate buffered saline (PBS), pH 7.4. Resuspension can be carried out using, e.g., equipment such as impellers connected to an overhead mixer, magnetic stir-bars, rocking shakers, etc.

A "soluble fraction," i.e., the soluble supernatant obtained after centrifugation of a lysate, and an "insoluble fraction," i.e., the pellet obtained after centrifugation of a lysate, result from lysing and centrifuging the cultures. These two fractions also can be referred to as a "first soluble fraction" and a "first insoluble fraction," respectively.

It is possible to obtain soluble IFN-β using extraction methods according to the invention, from expression cultures prepared by growing cultures under conditions in which the pH and the induction OD are not tightly controlled (see, e.g., Example 2). Optimization of the growth conditions as described herein results in substantially increased production of soluble IFN-β.

Non-Denaturing Extraction Process

It has been discovered that high levels of soluble interferon protein can be obtained from the insoluble fraction, using non-denaturing extraction methods of the present invention.

Non-denaturing extraction conditions identified as particularly useful for producing high levels of soluble recombinant interferon protein comprise: a mild detergent at a non-denaturing concentration, e.g., Zwittergent 3-14 (0.5 to 2% w/v); a chaotropic agent, e.g., urea (0-2M), and a cosmotropic salt, e.g., NaCl (0-2M), at a buffer pH of 6.5 to 8.5 and a solids concentration of 5-20% w/v.

After obtaining the soluble fraction and insoluble fraction, as described above, the soluble recombinant interferon protein is extracted from the insoluble fraction by incubating the resuspended insoluble fraction under the non-denaturing extraction conditions described herein. After incubation, the extracted mixture is centrifuged to produce an "extract supernatant" (the soluble supernatant fraction obtained after extraction containing solubilized recombinant protein) and an "extract pellet" (the insoluble pellet fraction obtained after extraction). These fractions can also be referred to as the "second soluble fraction" and the "second insoluble fraction."

Extraction Conditions

Many different parameters for the extraction conditions were evaluated for their effect on the amount of soluble protein observed in the extract supernatant, as described in Example 3 herein. It was found that soluble interferon protein was observed when the extraction conditions comprised any of a number of different detergents, at varying concentrations, as well as when other parameters were varied. However, certain parameters had a particularly striking effect on the amount of soluble protein produced.

Specifically, extraction conditions comprising Zwitterionic detergents (Zwittergents) gave the best soluble protein yields. In particular, use of the Zwitterionic detergents, Zwittergent 3-08, Zwittergent 3-10, Zwittergent 3-12, and especially Zwittergent 3-14, resulted in the highest yields. N-Lauroylsarcosine (NLS) gave a notably high yield, however the soluble protein obtained was found to be inactive based on an affinity assay (Sepharose blue affinity column binding). Therefore, the term "mild detergents" as used herein is intended not to include N-lauroylsarcosine.

The detergents were tested at non-denaturing concentrations. It was found that a concentration of Zwittergent 3-14 (3-(N,N-dimethylmyristylammonio) propanesulfonate) of at least 0.5% (w/v), and preferably 1%, well above its critical micelle concentration (which is 0.01%) provides the most efficient extraction of soluble interferon protein.

Therefore, use of non-denaturing concentrations of mild detergents, particularly Zwitterionic detergents, more particularly Zwittergent 3-08, Zwittergent 3-10, Zwittergent 3-12, and Zwittergent 3-14, more particularly Zwittergent 3-14, and not NLS, is contemplated for use in the extraction conditions of the invention.

In other embodiments of the invention, the non-denaturing extraction conditions comprise a concentration of about 0.5% to about 2% (w/v) Zwittergent 3-14. In embodiments, the w/v concentration of Zwittergent 3-14 is about 0.5% to about 1%, about 1% to about 1.5%, about 1.5% to about 2%, or about 1% to about 2%. In certain embodiments, the w/v concentration of Zwittergent 3-14 is about 0.5%, about 0.6%, about 0.7%, about 0.8%, about 0.9%, about 1.0%, about 1.1%, about 1.2%, about 1.3%, about 1.4%, about 1.5%, about 1.6%, about 1.7%, about 1.8%, about 1.9%, or about 2.0%.

In other embodiments of the invention, non-denaturing extraction conditions comprise a concentration of about 0.5% to about 2% (w/v) Zwittergent 3-08, Zwittergent 3-10, or Zwittergent 3-12. In embodiments, the w/v concentration of Zwittergent 3-08, Zwittergent 3-10, or Zwittergent 3-12 is about 0.5% to about 1%, about 1% to about 1.5%, about 1.5% to about 2%, or about 1% to about 2%. In certain embodiments, the w/v concentration of Zwittergent 3-08, Zwittergent 3-10, or Zwittergent 3-12 is about 0.5%, about 0.6%, about 0.7%, about 0.8%, about 0.9%, about 1.0%, about 1.1%, about 1.2%, about 1.3%, about 1.4%, about 1.5%, about 1.6%, about 1.7%, about 1.8%, about 1.9%, or about 2.0%.

A mild detergent does not cause protein unfolding at low levels, e.g., 2% or less. For example, SDS and NLS are typically considered stronger detergents, as they can denature proteins at these levels. A non-denaturing concentration indicates a concentration of a reagent at which proteins are not denatured. Proteins that are not denatured during processing do not require refolding.

In embodiments, non-denaturing extraction conditions of the present invention comprise about 0.5 to about 2% Zwittergent 3-14; about 0 to about 2 M urea; about 0 to about 2 M NaCl; and wherein the pH is about 6.5 to about 8.5.

The following table lists examples of common detergents, including ionic, non-ionic, and zwitter-ionic detergents, and their properties. An important characteristic of a detergent is its critical micelle concentration (CMC), which relates to its protein solubilization capability as well as the ease of subsequent removal of detergents from protein solutions.

TABLE 1

Examples of Detergents

| Detergent | Monomer, MW Da | Micelle, MW Da | CMC % (w/v) | CMC mM |
|---|---|---|---|---|
| Zwittergent 3-14 | 364 | 30,000 | 0.004-0.015 (0.011) | 0.1-0.4 (0.3) |
| Tween-20 | 1228 | | 0.007 | 0.059 |
| Tween-80 | 1310 | 76,000 | 0.0016 | 0.012 |
| Triton X-100 | 650 | 90,000 | 0.013-0.06 (0.021) | 0.2-0.9 (0.3) |
| Sodium Deoxycholate | 432 | 4,200 | 0.21 | 5 |
| Sodium Lauroylsarcosine | 293 | 600 | 0.4 | 13.7 |
| NDSB | 195 | N/A | N/A | N/A |
| NP-40 | 617 | 90000 | 0.003-0.018, | 0.05-0.3 |
| CHAPS | 615 | 6,000 | 0.37-0.62 | 6-10 |
| Octyl-β-glucopyranoside | 292 | 8,000 | 0.73 | 23 |

TABLE 2

Physical Properties of Zwitterionic Detergents

| Detergent | Monomer, MW Da | Micelle, MW Da | CMC % (w/v) | CMC mM |
|---|---|---|---|---|
| Zwittergent 3-08 | 280 | — | 9.2 | 330 |
| Zwittergent 3-10 | 308 | 12,500 | 0.77-1.23 | 25-40 |
| Zwittergent 3-12 | 336 | 18,500 | 0.067-0.134 | 2-4 |
| Zwittergent 3-14 | 364 | 30,000 | 0.004-0.015 (0.011) | 0.1-0.4 (0.3) |
| Zwittergent 3-16 | 392 | 60,000 | 0.0004-0.0024 | 0.01-0.06 |

It was further observed that when the non-denaturing extraction conditions comprised the combination of a chaotropic agent, urea, a cosmotropic salt, NaCl, Zwittergent 3-14, and an appropriate buffer range, the extraction yield was increased several-fold compared to the use of Zwittergent 3-14 alone (see Example 3).

TABLE 3

Selected concentration ranges of extraction components

| Component | Permissible Conc. Range | Selected Conc. |
|---|---|---|
| Zwittergent 3-14 | 0.5-2% (w/v) | 1% |
| Urea | 0-2M | 2M |
| NaCl | 0-2M | 2M |
| Solid Conc. | 5-20% (w/v) | 5% |
| Buffer pH | 6.5-8.5 | 8.2 |

Chaotropic agents disrupt the 3-dimensional structure of a protein or nucleic acid, causing denaturation. In embodiments, the non-denaturing extraction conditions comprise low, non-denaturing concentrations of chaotropic agents, e.g., urea or guanidinium hydrochloride. In embodiments, the non-denaturing extraction conditions comprise urea at a concentration of about 0.5M to about 2M or higher. We observed that 6M urea denatures IFN-β. Typically, non-denaturing concentrations of urea or guanidinium hydrochloride are below 3M. In embodiments, the non-denaturing extraction conditions comprise urea at a concentration of about 0.5 to about 1M, about 1 to about 1.5M, about 1.5 to about 2M, about 1 to about 2M, about 0.5M, about 0.6M, about 0.7M, about 0.8M, about 0.9M, about 1.0M, about 1.1M, about 1.2M, about 1.3M, about 1.4M, about 1.5M, about 1.6M, about 1.7M, about 1.8M, about 1.9M, or about 2.0M. In other embodiments, the extraction conditions comprise guanidinium hydrochloride at a concentration of 0.5 to 2M. In embodiments, extraction conditions comprise guanidinium hydrochloride at a concentration of 0.5 to 1M, 1 to 1.5M, 1.5 to 2M, 1 to 2M, 0.5M, about 0.6M, about 0.7M, about 0.8M, about 0.9M, about 1.0M, about 1.1M, about 1.2M, about 1.3M, about 1.4M, about 1.5M, about 1.6M, about 1.7M, about 1.8M, about 1.9M, or about 2.0M.

Cosmotropic salts contribute to the stability and structure of water-water interactions. Cosmotropes cause water molecules to favorably interact, which also stabilizes intermolecular interactions in macromolecules such as proteins. Any such appropriate agent, as known in the art, can be used in the extraction conditions of the present invention. In embodiments, the non-denaturing extraction conditions comprise a cosmotropic salt selected from NaCl, KCl, and $(NH_4)_2SO_4$. In certain embodiments, NaCl is present at a concentration of about 0.15M to about 2M. In embodiments, NaCl is present in the extraction conditions at a concentration of about 0.15 to about 0.5M, about 0.5 to about 0.75M, about 0.75M to about 1M, about 1M to about 1.25M, about 1.25M to about 1.5M, about 1.5M to about 1.75M, about 1.75M to about 2M, about 0.15M to about 1M, about 1M to about 1.5M, about 1.5M to about 2M, about 1M to about 2M, about 0.15M, about 0.25M, about 0.5M, about 0.6M, about 0.7M, about 0.8M, about 0.9M, about 1.0M, about 1.1M, about 1.2M, about 1.3M, about 1.4M, about 1.5M, about 1.6M, about 1.7M, about 1.8M, about 1.85M, about 1.9M, or about 2.0M.

In other embodiments, KCl is present in the non-denaturing extraction conditions at a concentration of about 0.15 to about 0.5M, about 0.5 to about 0.75M, about 0.75M to about 1M, about 1M to about 1.25M, about 1.25M to about 1.5M, about 1.5M to about 1.75M, about 1.75M to about 2M, about 0.15M to about 1M, about 1M to about 1.5M, about 1.5M to about 2M, about 1M to about 2M, about 0.15M, about 0.25M, about 0.5M, about 0.6M, about 0.7M, about 0.8M, about 0.9M, about 1.0M, about 1.1M, about 1.2M, about 1.3M, about 1.4M, about 1.5M, about 1.6M, about 1.7M, about 1.8M, about 1.85M, about 1.9M, or about 2.0M.

In other embodiments, $(NH_4)_2SO_4$ is present in the non-denaturing extraction conditions at a concentration of about 0.15 to about 0.5M, about 0.5 to about 0.75M, about 0.75M to about 1M, about 1M to about 1.25M, about 1.25M to about 1.5M, about 1.5M to about 1.75M, about 1.75M to about 2M, about 0.15M to about 1M, about 1M to about 1.5M, about 1.5M to about 2M, about 1M to about 2M, about 0.15M, about 0.25M, about 0.5M, about 0.6M, about 0.7M, about 0.8M, about 0.9M, about 1.0M, about 1.1M, about 1.2M, about 1.3M, about 1.4M, about 1.5M, about 1.6M, about 1.7M, about 1.8M, about 1.85M, about 1.9M, or about 2.0M.

The extraction conditions were found to be most effective when the pH was maintained within a range of 6.5 to 8.5. Useful pH buffers are those recommended in standard protein purification texts (e.g., Protein Purification: Principles and Practice, by Robert Scopes (Springer, 1993)) can be used here, including Tris, Bis-Tris, phosphate, citrate, acetate, glycine, diethanolamine, 2-amino-2-methyl-1,3-propanediol, triethanolamine, imidazole, histidine, pyridine, etc. Many buffers have been described in the literature and are commercially available. In embodiments, the pH of the non-denaturing extraction conditions is about 6.5, about 6.6, about 6.7, about 6.8, about 6.9, about 7.0, about 7.1, about 7.2, about 7.3, about 7.4, about 7.5, about 7.6, about 7.8, about 7.9, about 8.0, about 8.1, about 8.2, about 8.3, about 8.4, or about 8.5. In other embodiments, the pH is about 6.5 to about 6.8, about 6.6 to about 6.9, about 6.7 to about 7.0, about 6.8 to about 7.1, about 6.9 to about 7.2, about 7.0 to about 7.3, about 7.1 to about 7.4, about 7.2 to about 7.5, about 7.3 to about 7.6, about 7.4 to about 7.7, about 7.5 to about 7.8, about 7.6 to about 7.9, about 7.8 to about 8.1, about 7.9 to about 8.2, about 8.0 to about 8.3, about 8.1 to about 8.4 or about 8.2 to about 8.5. In other embodiments, the pH is about 6.5 to about 7.0, about 7.0 to about 7.5, or about 7.5 to about 8.0.

The solids concentration in the non-denaturing extraction conditions was also varied. This parameter represents the amount of solid material in the extract incubation mixture. Solids concentration can be determined by weighing the wet pellet (i.e., the insoluble fraction), and comparing this weight with the total weight of the extraction mixture. Specific solids concentrations are achieved by concentrating or diluting the insoluble fraction. High extraction yields were observed across a range of solids concentrations of 5% to 40% (w/v). In embodiments of the invention, the solids in the non-denaturing extraction conditions are present at a w/v concentration of about 5%, about 7.5%, about 10%, about 12.5%, about 15%, about 17.5%, about 20%, about 22.5%, about 25%, about 27.5%, about 30%, about 32.5%, about 35%, about 37.5%, or about 40%. In other embodiments of the invention, the solids in the non-denaturing extraction conditions are present at a w/v concentration of about 5% to about 7.5%, about 7.5% to about 10%, about 10% to about 12.5%, about 12.5% to about 15%, about 15% to about 17.5%, about 17.5% to about 20%, about 20% to about 22.5%, about 22.5% to about 25%, about 25% to about 27.5%, about 27.5% to about 30%, about 30% to about 32.5%, about 32.5% to about 35%, about 35% to about 37.5%, about 37.5% to about 40%, about 5% to about 10%, about 10% to about 15%, about 15% to about 20%, about 20% to about 25%, about 25% to about 30%, about 35% to about 40%, about 5% to about 15%, about 5% to about 25%, about 5% to about 30%, about 5% to about 35%, about 10% to about 20%, about 20% to about 30%, about 30% to about 40%, about 5% to about 20%, or about 20% to about 40%.

In embodiments, the extraction methods of the invention are combined with simultaneous enrichment techniques such as adsorption to further enhance protein yield.

The solubilized protein can be isolated or purified from other protein and cellular debris by, for example, centrifugation and/or chromatography such as size exclusion, anion or cation exchange, hydrophobic interaction, or affinity chromatography.

Interferons

Human interferons have been classified into three major types. Interferon type I: Type I IFNs bind to a specific cell surface receptor complex known as the IFN-α receptor (IFNAR) that consists of IFNAR1 and IFNAR2 chains.

Human type I interferons include are IFN-α, IFN-β, IFN-κ, and IFN-ω and IFN-ε. Interferon type II: Type II IFNs (human IFN-γ) binds to IFNGR. Interferon type III: type III interferons signal through a receptor complex consisting of IL10R2 (also called CRF2-4) and IFNLR1 (also called CRF2-12).

Human Type I interferon appears to bind to two-receptor subunits, IFNAR-1 and -2, which are widely distributed on the cell surface of various cell types. Ligand involvement leads to the induction of the phosphorylation of tyrosine kinases TYK2 and JAK-1, which are coupled to IFNAR-1 and -2 respectively. Once phosphorylated, STAT proteins are released from the receptor and form homodimers as well as heterodimers. Once released, the dimers of STAT associate with interferon Responsive Factor 9 (IRF-9), a DNA binding protein, forming a complex called IFN-stimulated gene factor-3 (ISGF-3), that migrates into the nucleus. Next, the ISGF-3 complex binds to a DNA element existing in the upstream of all IFN inducible genes. Type 1 interferons are described extensively in the literature, e.g., in U.S. Pat. No. 7,625,555, "Recombinant human interferon-like proteins, incorporated herein by reference."

Type 1 IFNs have substantial structural similarity, as evidenced by their sequences and their shared receptor binding capacity. According to Kontsek, P., 1994, "Human type I interferons: structure and function," Acta Virol. 38(6): 345-60, incorporated by reference herein, human type I interferons (13 had been reported at the time) have a 20% overall sequence homology, which determines identical secondary and tertiary folding of polypeptides. Further, Kontsek reports that three-dimensional models suggest that the globular structure of type I IFNs consists of a bundle of 5 α-helices, which might form two polypeptide domains. Disulfide bond Cys 29-Cys 139 stabilizes both domains in a bioactive configuration. Two conservative hydrophilic regions associated with the amino acids (aa) 30-41 and 120-145 are thought to constitute the basic framework of receptor recognition site in type I IFNs, and the different spectra of biological effects among human type I IFNs are speculated to be due to subtle sequential heterogeneity in the segments aa 30-41 and 120-145, and the variable hydrophilic aa regions 23-26, 68-85 and 112-121. A later report by Oritani, et al., 2001, "Type I interferons and limitin: a comparison of structures, receptors, and functions," Cytokine Growth Factor Rev 12(4):337-48, incorporated by reference herein, describes family members IFN-α, IFN-β, IFN-pi, and IFN-tau. The paper also reports that IFN-α and IFN-β have a globular structure composed of five a-helices, and discusses comparative sequence analyses, a prototypic three-dimensional structure, analysis with monoclonal antibodies, and construction of hybrid molecules and site directed mutagenesis.

Production of any Type 1 interferon protein using the methods of the present invention is contemplated. Type 1 interferon proteins that can be produced using the methods of the invention, include, but not limited to, human IFN-α 2a and 2b, human IFN-β 1b, human IFN-κ (e.g., NM_020124, AAK63835, and described by LaFleur, et al., 2001, "Interferon-kappa, a novel type I interferon expressed in human keratinocytes," J. Biol. Chem. 276 (43), 39765-39771, incorporated herein by reference), and human IFN-w (e.g., NM_002177, NP_002168, and described in U.S. Pat. No. 7,470,675, "Methods for treating cancer using interferon-ω-expressing polynucleotides," incorporated by reference herein in its entirety). Production of IFN-τ using the methods of the invention is also contemplated. Amino acid and nucleic acid sequences are publicly available, e.g., from GenBank.

Fourteen subtypes of IFN-α proteins have been described: IFNA1, IFNA2, IFNA4, IFNA5, IFNA6, IFNA7, IFNA8, IFNA10, IFNA13, IFNA14, IFNA16, IFNA17, IFNA21. IFN-α is made synthetically as therapeutic agent, as pegylated interferon alfa-2a and pegylated interferon alfa-2b.

IFN-β (IFNB1, or IFN-β 1b) is the main β subtype (see, e.g., GenBank NP002167.1, which provides the mature peptide sequence). Betaseron is an analogue of human IFN-β in which serine was genetically engineered to substitute for cysteine at position 17, is known as IFN-β 1b C17S (described in U.S. Pat. No. 4,588,585, "Human recombinant cysteine depleted interferon-β muteins," incorporated herein by reference). The molecule is a small polypeptide of 165 amino acids with a single disulphide bond, and is produced as a non-glycosylated protein.

IFN-τ is described, and sequences of IFN-τ disclosed, e.g., in U.S. Pat. No. 7,214,367, "Orally-administered interferon-tau compositions and methods," incorporated herein by reference in its entirety.

A number of Type 1 IFNs have been approved by the FDA for use in treating disease in humans. The following table lists examples of Type 1 interferon drugs. In embodiments of the invention, any of these drugs are produced using the methods as claimed or described herein.

TABLE 4

Examples of Type 1 interferon drugs.

| Generic name | Trade name |
| --- | --- |
| Interferon α 2a | Roferon A |
| PEGylated interferon α 2a | Pegasys |
| PEGylated interferon α 2a | Reiferon Retard |
| Interferon α 2b | Intron A/Reliferon |
| PEGylated interferon α 2b | PegIntron |
| Human leukocyte Interferon-α (HuIFN-α-Le) | Multiferon |
| Interferon β 1a, liquid form | Rebif |
| Interferon β 1a | lyophilized Avonex |
| Interferon β 1b | Betaseron/Betaferon |

In embodiments, variants and modifications of Type 1 interferon proteins are produced using the methods of the present invention. For example, IFN-β variants are described in U.S. Pat. No. 6,531,122 "Interferon-β variants and conjugates," and U.S. Pat. No. 7,625,555, both incorporated by reference herein. Conjugates include pegylated Type 1 interferons, e.g., the PEGylated agents shown in Table 4, and interferons linked to non-peptide moieties.

The methods of the invention are expected to be useful for all Type 1 interferons, due to their structural similarities. Certain structurally unrelated proteins, for example, human GCSF, have been found poor candidates for producing using the methods of the present invention. When GCSF was produced and extracted using methods as described herein, less than 5% of the amount of GCSF protein in the insoluble fraction was extracted as soluble protein (data not shown).

In general, with respect to an amino acid sequence, the term "modification" includes substitutions, insertions, elongations, deletions, and derivatizations alone or in combination. In some embodiments, the peptides may include one or more modifications of a "non-essential" amino acid residue. In this context, a "non-essential" amino acid residue is a residue that can be altered, e.g., deleted or substituted, in the novel amino acid sequence without abolishing or substantially reducing the activity (e.g., the agonist activity) of the peptide (e.g., the analog peptide). In some embodiments, the peptides may include one or more modifications of an "essential" amino acid residue. In this context, an "essential" amino acid residue is a residue that when altered, e.g., deleted or substituted, in the novel amino acid sequence the activity of the reference peptide is substantially reduced or abolished. In such embodiments where an essential amino acid residue is altered, the modified peptide may possess an activity of a Type 1 interferon of interest in the methods provided. The substitutions, insertions and deletions may be at the N-terminal or C-terminal end, or may be at internal portions of the protein. By way of example, the protein may include 1, 2, 3, 4, 5, 6, 7, 8, 9, 10, or more substitutions, both in a consecutive manner or spaced throughout the peptide molecule. Alone or in combination with the substitutions, the peptide may include 1, 2, 3, 4, 5, 6, 7, 8, 9, 10, or more insertions, again either in consecutive manner or spaced throughout the peptide molecule. The peptide, alone or in combination with the substitutions and/or insertions, may also include 1, 2, 3, 4, 5, 6, 7, 8, 9, 10, or more deletions, again either in consecutive manner or spaced throughout the peptide molecule. The peptide, alone or in combination with the substitutions, insertions and/or deletions, may also include 1, 2, 3, 4, 5, 6, 7, 8, 9, 10, or more amino acid additions.

Substitutions include conservative amino acid substitutions. A "conservative amino acid substitution" is one in which the amino acid residue is replaced with an amino acid residue having a similar side chain, or physicochemical characteristics (e.g., electrostatic, hydrogen bonding, isosteric, hydrophobic features). The amino acids may be naturally occurring or nonnatural (unnatural). Families of amino acid residues having similar side chains are known in the art. These families include amino acids with basic side chains (e.g. lysine, arginine, histidine), acidic side chains (e.g., aspartic acid, glutamic acid), uncharged polar side chains (e.g., glycine, asparagine, glutamine, serine, threonine, tyrosine, methionine, cysteine), nonpolar side chains (e.g., alanine, valine, leucine, isoleucine, proline, phenylalanine, tryptophan), β-branched side chains (e.g., threonine, valine, isoleucine) and aromatic side chains (e.g., tyrosine, phenylalanine, tryptophan, histidine). Substitutions may also include non-conservative changes.

Methods for Selecting Optimal Extraction Conditions

In embodiments of the present invention, the results of the statistical analysis as set forth in FIG. 4B are used to further optimize extraction conditions within the ranges of parameter values provided. High level soluble protein production of all Type 1 interferons is expected to be observed when practicing the invention using any values within the ranges set forth. Nonetheless, it is within the capacity of one of skill in the art to utilize the tool represented by FIG. 4B to optimize the extraction conditions to fit the need at hand.

Evaluation of Product

Protein Yield

Protein yield in the insoluble and soluble fractions as described herein can be determined by methods known to those of skill in the art, for example, by capillary gel electrophoresis (CGE), and Western blot analysis.

Useful measures of protein yield include, e.g., the amount of recombinant protein per culture volume (e.g., grams or milligrams of protein/liter of culture), percent or fraction of recombinant protein measured in the insoluble pellet obtained after lysis (e.g., amount of recombinant protein in extract supernatant/amount of protein in insoluble fraction), percent or fraction of active protein (e.g., amount of active protein/amount protein used in the assay), percent or fraction of total cell protein (tcp), amount of protein/cell, and percent dry biomass. In embodiments, the measure of protein yield as described herein is based on the amount of soluble protein or the amount of active protein, or both, obtained.

In embodiments, the methods of the present invention can be used to obtain an extracted recombinant protein yield of about 0.3 grams per liter to about 10 grams per liter. In certain embodiments, the extracted recombinant protein yield is about 0.3 grams per liter to about 1 gram per liter, about 1 gram per liter to about 2 grams per liter, about 2 grams per liter to about 3 grams per liter, about 3 grams per liter to about 4 grams per liter, about 4 grams per liter to about 5 grams per liter, about 5 grams per liter to about 6 grams per liter, about 6 grams per liter to about 7 grams per liter, about 7 grams per liter to about 8 grams per liter, about 8 grams per liter to about 9 grams per liter, or about 9 grams per liter to about 10 grams per liter. In embodiments, the extracted protein yield is about 1 gram per liter to about 3 grams per liter, about 2 grams per liter to about 4 grams per liter, about 3 grams per liter to about 5 grams per liter, about 4 grams per liter to about 6 grams per liter, about 5 grams per liter to about 7 grams per liter, about 6 grams per liter to about 8 grams per liter, about 7 grams per liter to about 9 grams per liter, or about 8 grams per liter to about 10 grams per liter. In embodiments, the extracted protein yield is about 0.5 grams per liter to about 4 grams per liter, 1 gram per liter to about 5 grams per liter, 2 grams per liter to about 6 grams per liter, about 3 grams per liter to about 7 grams per liter, about 4 grams per liter to about 8 grams per liter, about 5 grams per liter to about 9 grams per liter, or about 6 grams per liter to about 10 grams per liter. In embodiments, the extracted protein yield is about 0.5 gram per liter to about 5 grams per liter, about 1 grams per liter to about 6 grams per liter, about 2 grams per liter to about 7 grams per liter, about 3 grams per liter to about 8 grams per liter, about 4 grams per liter to about 9 grams per liter, or about 5 grams per liter to about 10 grams per liter.

In embodiments, the amount of recombinant interferon protein detected in the extracted supernatant fraction is about 10% to about 95% of the amount of the recombinant interferon protein detected in the insoluble fraction. In embodiments, this amount is about 10%, about 15%, about 20%, about 25%, about 30%, about 35%, about 40%, about 45%, about 50%, about 55%, about 60%, about 65%, about 70%, about 75%, about 80%, about 85%, about 90%, or about 95%. In embodiments, this amount is about 10% to about 20%, 20% to about 50%, about 25% to about 50%, about 25% to about 50%, about 25% to about 95%, about 30% to about 50%, about 30% to about 40%, about 30% to about 60%, about 30% to about 70%, about 35% to about 50%, about 35% to about 70%, about 35% to about 75%, about 35% to about 95%, about 40% to about 50%, about 40% to about 95%, about 50% to about 75%, about 50% to about 95%, or about 70% to about 95%.

The protein yield measured in the unextracted insoluble fraction is typically higher than that in the extract supernatant, as material is lost during the extraction procedure. Yields from fermentation cultures are typically higher than those from smaller HTP cultures.

"Percent total cell protein" is the amount of protein or polypeptide in the host cell as a percentage of aggregate cellular protein. The determination of the percent total cell protein is well known in the art.

In embodiments, the amount of interferon protein detected in the extracted supernatant fraction produced is about 1% to about 75% of the total cell protein. In certain embodiments, the recombinant protein produced is about 1%, about 2%, about 3%, about 4%, about 5%, about 10%, about 15%, about 20%, about 25%, about 30%, about 35%, about 40%, about 45%, about 50%, about 55%, about 60%, about 65%, about 70%, about 75%, about 1% to about 5%, about 1% to about 10%, about 1% to about 20%, about 1% to about 30%, about 1% to about 40%, about 1% to about 50%, about 1% to about 60%, about 1% to about 75%, about 2% to about 5%, about 2% to about 10%, about 2% to about 20%, about 2% to about 30%, about 2% to about 40%, about 2% to about 50%, about 2% to about 60%, about 2% to about 75%, about 3% to about 5%, about 3% to about 10%, about 3% to about 20%, about 3% to about 30%, about 3% to about 40%, about 3% to about 50%, about 3% to about 60%, about 3% to about 75%, about 4% to about 10%, about 4% to about 20%, about 4% to about 30%, about 4% to about 40%, about 4% to about 50%, about 4% to about 60%, about 4% to about 75%, about 5% to about 10%, about 5% to about 20%, about 5% to about 30%, about 5% to about 40%, about 5% to about 50%, about 5% to about 60%, about 5% to about 75%, about 10% to about 20%, about 10% to about 30%, about 10% to about 40%, about 10% to about 50%, about 10% to about 60%, about 10% to about 75%, about 20% to about 30%, about 20% to about 40%, about 20% to about 50%, about 20% to about 60%, about 20% to about 75%, about 30% to about 40%, about 30% to about 50%, about 30% to about 60%, about 30% to about 75%, about 40% to about 50%, about 40% to about 60%, about 40% to about 75%, about 50% to about 60%, about 50% to about 75%, about 60% to about 75%, or about 70% to about 75%, of the total cell protein.

Solubility and Activity

The "solubility" and "activity" of a protein, though related qualities, are generally determined by different means. Solubility of a protein, particularly a hydrophobic protein, indicates that hydrophobic amino acid residues are improperly located on the outside of the folded protein. Protein activity, which can be evaluated using different methods, e.g., as described below, is another indicator of proper protein conformation. "Soluble, active, or both" as used herein, refers to protein that is determined to be soluble, active, or both soluble and active, by methods known to those of skill in the art.

Interferon Activity Assays

Assays for evaluating interferon protein activity are known in the art and include binding activity assays that measure binding of interferon to a standard ligand, e.g., a Blue sepharose column or a specific antibody column.

Biological activity of interferons can be quantitated using known assays, many of which are available commercially in kits. Most or all interferon species have been shown to exert a similar spectrum of in vitro biological activities in responsive cells, despite the existence of different receptors for type I and type II IFN. Biological activities induced by IFN include antiviral activity, which is mediated via cell receptors and is dependent on the activation of signaling pathways, the expression of specific gene products, and the development of antiviral mechanisms. Sensitivity of cells to IFN-mediated antiviral activity is variable, and depends on a number of factors including cell type, expression of IFN receptors and downstream effector response elements, effectiveness of antiviral mechanisms, and the type of virus used to infect cells.

Biological activity assays include, e.g., cytopathic effect assays (CPE), antiviral activity assays, assays that measure inhibition of cell proliferation, regulation of functional cellular activities, regulation of cellular differentiation and immunomodulation. Reporter gene assays include the luciferase reporter cell-based assay described herein in the Examples. In a reporter gene assay, the promoter region of an IFN responsive gene is linked with a heterologous reporter gene, for example, firefly luciferase or alkaline phosphatase, and transfected into an IFN-sensitive cell line. Stably transfected cell lines exposed to IFN increase expression of the reporter gene product in direct relation to the dose of IFN, the readout being a measure of this product's enzymic action. Many activity assay tools and kits are available commercially. Biological assays for interferons are described, e.g., by Meager A, "Biological assays for interferons," 1 Mar. 2002, J. Immunol. Methods 261(1-2):21-36, incorporated herein by reference.

In embodiments, activity is represented by the % active protein in the extract supernatant as compared with the total amount assayed. This is based on the amount of protein determined to be active by the assay relative to the total amount of protein used in assay. In other embodiments, activity is represented by the % activity level of the protein compared to a standard, e.g., native protein. This is based on the amount of active protein in supernatant extract sample relative to the amount of active protein in a standard sample (where the same amount of protein from each sample is used in assay).

In embodiments, about 40% to about 100% of the recombinant interferon protein is determined to be active. In embodiments, about 40%, about 50%, about 60%, about 70%, about 80%, about 90%, or about 100% of the recombinant interferon protein is determined to be active. In embodiments, about 40% to about 50%, about 50% to about 60%, about 60% to about 70%, about 70% to about 80%, about 80% to about 90%, about 90% to about 100%, about 50% to about 100%, about 60% to about 100%, about 70% to about 100%, about 80% to about 100%, about 40% to about 90%, about 40% to about 95%, about 50% to about 90%, about 50% to about 95%, about 50% to about 100%, about 60% to about 90%, about 60% to about 95%, about 60% to about 100%, about 70% to about 90%, about 70% to about 95%, about 70% to about 100%, or about 70% to about 100% of the recombinant interferon protein is determined to be active.

In other embodiments, about 75% to about 100% of the recombinant interferon protein is determined to be active. In embodiments, about 75% to about 80%, about 75% to about 85%, about 75% to about 90%, about 75% to about 95%, about 80% to about 85%, about 80% to about 90%, about 80% to about 95%, about 80% to about 100%, about 85% to about 90%, about 85% to about 95%, about 85% to about 100%, about 90% to about 95%, about 90% to about 100%, or about 95% to about 100% of the recombinant interferon protein is determined to be active.

Expression Systems

Methods for expressing heterologous proteins, including useful regulatory sequences (e.g., promoters, secretion leaders, and ribosome binding sites), in *Pseudomonas* host cells, as well as host cells useful in the methods of the present invention, are described, e.g., in U.S. Pat. App. Pub. No. 2008/0269070 and U.S. patent application Ser. No. 12/610,207, both titled "Method for Rapidly Screening Microbial Hosts to Identify Certain Strains with Improved Yield and/or Quality in the Expression of Heterologous Proteins," U.S. Pat. App. Pub. No. 2006/0040352, "Expression of Mammalian Proteins in *Pseudomonas Fluorescens*," and U.S. Pat. App. Pub. No. 2006/0110747, "Process for Improved Protein Expression by Strain Engineering," all incorporated herein by reference in their entirety. These publications also describe bacterial host strains useful in practicing the methods of the invention, that have been engineered to overexpress folding modulators or wherein protease mutations have been introduced, in order to increase heterologous protein expression. Sequence leaders are described in detail in U.S. Patent App. Pub. No. 2008/0193974, "Bacterial leader sequences for increased expression," and U.S. Pat. App. Pub. No. 2006/0008877, "Expression systems with Sec-secretion," both incorporated herein by reference in their entirety, as well as in U.S. patent application Ser. No. 12/610,207.

Promoters

The promoters used in accordance with the present invention may be constitutive promoters or regulated promoters. Common examples of useful regulated promoters include those of the family derived from the lac promoter (i.e. the lacZ promoter), especially the tac and trc promoters described in U.S. Pat. No. 4,551,433 to DeBoer, as well as Ptac16, Ptac17, PtacII, PlacUV5, and the T7lac promoter. In one embodiment, the promoter is not derived from the host cell organism. In certain embodiments, the promoter is derived from an *E. coli* organism.

Inducible promoter sequences can be used to regulate expression of interferons in accordance with the methods of the invention. In embodiments, inducible promoters useful in the methods of the present invention include those of the family derived from the lac promoter (i.e. the lacZ promoter), especially the tac and trc promoters described in U.S. Pat. No. 4,551,433 to DeBoer, as well as Ptac16, Ptac17, PtacII, PlacUV5, and the T7lac promoter. In one embodiment, the promoter is not derived from the host cell organism. In certain embodiments, the promoter is derived from an *E. coli* organism.

Common examples of non-lac-type promoters useful in expression systems according to the present invention include, e.g., those listed in Table 5.

TABLE 5

Examples of non-lac Promoters

| Promoter | Inducer |
| --- | --- |
| $P_R$ | High temperature |
| $P_L$ | High temperature |
| Pm | Alkyl- or halo-benzoates |
| Pu | Alkyl- or halo-toluenes |
| Psal | Salicylates |

See, e.g.: J. Sanchez-Romero & V. De Lorenzo (1999) Manual of Industrial Microbiology and Biotechnology (A. Demain & J. Davies, eds.) pp. 460-74 (ASM Press, Washington, D.C.); H. Schweizer (2001) Current Opinion in Biotechnology, 12:439-445; and R. Slater & R. Williams (2000 Molecular Biology and Biotechnology (J. Walker & R. Rapley, eds.) pp. 125-54 (The Royal Society of Chemistry, Cambridge, UK)). A promoter having the nucleotide sequence of a promoter native to the selected bacterial host cell also may be used to control expression of the transgene encoding the target polypeptide, e.g, a *Pseudomonas* anthranilate or benzoate operon promoter (Pant, Pben). Tandem promoters may also be used in which more than one promoter is covalently attached to another, whether the same or different in sequence, e.g., a Pant-Pben tandem promoter (interpromoter hybrid) or a Plac-Plac tandem promoter, or whether derived from the same or different organisms.

Regulated promoters utilize promoter regulatory proteins in order to control transcription of the gene of which the promoter is a part. Where a regulated promoter is used herein, a corresponding promoter regulatory protein will also be part of an expression system according to the present invention. Examples of promoter regulatory proteins include: activator proteins, e.g., *E. coli* catabolite activator protein, MalT protein; AraC family transcriptional activators; repressor proteins, e.g., *E. coli* LacI proteins; and dual-function regulatory proteins, e.g., *E. coli* NagC protein. Many regulated-promoter/promoter-regulatory-protein pairs are known in the art. In one embodiment, the expression construct for the target protein(s) and the heterologous protein of interest are under the control of the same regulatory element.

Promoter regulatory proteins interact with an effector compound, i.e., a compound that reversibly or irreversibly associates with the regulatory protein so as to enable the protein to either release or bind to at least one DNA transcription regulatory region of the gene that is under the control of the promoter, thereby permitting or blocking the action of a transcriptase enzyme in initiating transcription of the gene. Effector compounds are classified as either inducers or co-repressors, and these compounds include native effector compounds and gratuitous inducer compounds. Many regulated-promoter/promoter-regulatory-protein/effector-compound trios are known in the art. Although an effector compound can be used throughout the cell culture or fermentation, in a preferred embodiment in which a regulated promoter is used, after growth of a desired quantity or density of host cell biomass, an appropriate effector compound is added to the culture to directly or indirectly result in expression of the desired gene(s) encoding the protein or polypeptide of interest.

In embodiments wherein a lac family promoter is utilized, a lacI gene can also be present in the system. The lacI gene, which is normally a constitutively expressed gene, encodes the Lac repressor protein LacI protein, which binds to the lac operator of lac family promoters. Thus, where a lac family promoter is utilized, the lacI gene can also be included and expressed in the expression system.

Promoter systems useful in *Pseudomonas* are described in the literature, e.g., in U.S. Pat. App. Pub. No. 2008/0269070, also referenced above.

Other Regulatory Elements

In embodiments, soluble proteins are present in either the cytoplasm or periplasm of the cell during production. Secretion leaders useful for targeting proteins are described elsewhere herein, and in U.S. Pat. App. Pub. No. 2008/0193974, U.S. Pat. App. Pub. No. 2006/0008877, and in U.S. patent application Ser. No. 12/610,207, referenced above.

An expression construct useful in practicing the methods of the present invention can include, in addition to the protein coding sequence, the following regulatory elements operably linked thereto: a promoter, a ribosome binding site (RBS), a transcription terminator, and translational start and stop signals. Useful RBSs can be obtained from any of the species useful as host cells in expression systems according to, e.g., U.S. Pat. App. Pub. No. 2008/0269070 and U.S. patent application Ser. No. 12/610,207. Many specific and a variety of consensus RBSs are known, e.g., those described in and referenced by D. Frishman et al., Gene 234(2):257-65 (8 Jul. 1999); and B. E. Suzek et al., Bioinformatics 17(12): 1123-30 (December 2001). In addition, either native or synthetic RBSs may be used, e.g., those described in: EP 0207459 (synthetic RBSs); O. Ikehata et al., Eur. J. Biochem. 181(3):563-70 (1989) (native RBS sequence of AAGGAAG). Further examples of methods, vectors, and translation and transcription elements, and other elements useful in the present invention are described in, e.g.: U.S. Pat. No. 5,055,294 to Gilroy and U.S. Pat. No. 5,128,130 to Gilroy et al.; U.S. Pat. No. 5,281,532 to Rammler et al.; U.S. Pat. Nos. 4,695,455 and 4,861,595 to Barnes et al.; U.S. Pat. No. 4,755,465 to Gray et al.; and U.S. Pat. No. 5,169,760 to Wilcox.

Host Strains

Bacterial hosts, including *Pseudomonas*, and closely related bacterial organisms are contemplated for use in practicing the methods of the invention. In certain embodiments, the *Pseudomonas* host cell is *Pseudomonas fluorescens*. The host cell can also be an *E. coli* cell.

*Pseudomonas* and closely related bacteria are generally part of the group defined as "Gram(−) Proteobacteria Subgroup 1" or "Gram-Negative Aerobic Rods and Cocci" (Buchanan and Gibbons (eds.) (1974) Bergey's Manual of Determinative Bacteriology, pp. 217-289). *Pseudomonas* host strains are described in the literature, e.g., in U.S. Pat. App. Pub. No. 2006/0040352, cited above.

For example, *Pseudomonas* hosts can include cells from the genus *Pseudomonas, Pseudomonas enalia* (ATCC 14393), *Pseudomonas nigrifaciensi* (ATCC 19375), and *Pseudomonas putrefaciens* (ATCC 8071), which have been reclassified respectively as *Alteromonas haloplanktis, Alteromonas nigrifaciens*, and *Alteromonas putrefaciens*. Similarly, e.g., *Pseudomonas acidovorans* (ATCC 15668) and *Pseudomonas testosteroni* (ATCC 11996) have since been reclassified as *Comamonas acidovorans* and *Comamonas testosteroni*, respectively; and *Pseudomonas nigrifaciens* (ATCC 19375) and *Pseudomonas piscicida* (ATCC 15057) have been reclassified respectively as *Pseudoalteromonas nigrifaciens* and *Pseudoalteromonas piscicida*.

The host cell can be selected from "Gram-negative Proteobacteria Subgroup 16." "Gram-negative Proteobacteria Subgroup 16" is defined as the group of Proteobacteria of the following *Pseudomonas* species (with the ATCC or other deposit numbers of exemplary strain(s) shown in parenthesis): *Pseudomonas abietaniphila* (ATCC 700689); *Pseudomonas aeruginosa* (ATCC 10145); *Pseudomonas alcaligenes* (ATCC 14909); *Pseudomonas anguilliseptica* (ATCC 33660); *Pseudomonas citronellolis* (ATCC 13674); *Pseudomonas flavescens* (ATCC 51555); *Pseudomonas mendocina* (ATCC 25411); *Pseudomonas nitroreducens* (ATCC 33634); *Pseudomonas oleovorans* (ATCC 8062); *Pseudomonas pseudoalcaligenes* (ATCC 17440); *Pseudomonas resinovorans* (ATCC 14235); *Pseudomonas straminea* (ATCC 33636); *Pseudomonas agarici* (ATCC 25941); *Pseudomonas alcaliphila; Pseudomonas alginovora; Pseudomonas andersonii; Pseudomonas asplenii* (ATCC 23835); *Pseudomonas azelaica* (ATCC 27162); *Pseudomonas beyerinckii* (ATCC 19372); *Pseudomonas borealis; Pseudomonas boreopolis* (ATCC 33662); *Pseudomonas brassicacearum; Pseudomonas butanovora* (ATCC 43655); *Pseudomonas cellulosa* (ATCC 55703); *Pseudomonas aurantiaca* (ATCC 33663); *Pseudomonas chlororaphis* (ATCC 9446, ATCC 13985, ATCC 17418, ATCC 17461); *Pseudomonas fragi* (ATCC 4973); *Pseudomonas lundensis* (ATCC 49968); *Pseudomonas taetrolens* (ATCC 4683); *Pseudomonas cissicola* (ATCC 33616); *Pseudomonas coronafaciens; Pseudomonas diterpeniphila; Pseudomonas elongata* (ATCC 10144); *Pseudomonasflectens* (ATCC 12775); *Pseudomonas azotoformans; Pseudomonas brenneri; Pseudomonas cedrella; Pseudomonas corrugata* (ATCC 29736); *Pseudomonas extremorientalis; Pseudomonas fluorescens* (ATCC 35858); *Pseudomonas gessardii; Pseudomonas libanensis; Pseudomonas mandelii* (ATCC 700871); *Pseudomonas marginalis* (ATCC 10844); *Pseudomonas migulae; Pseudomonas mucidolens* (ATCC 4685); *Pseudomonas orientalis; Pseudomonas rhodesiae; Pseudomonas synxantha* (ATCC 9890); *Pseudomonas tolaasii* (ATCC 33618); *Pseudomonas veronii* (ATCC 700474); *Pseudomonas frederiksbergensis; Pseudomonas geniculata* (ATCC 19374); *Pseudomonas gingeri; Pseudomonas graminis; Pseudomonas grimontii; Pseudomonas halodenitrificans; Pseudomonas halophila; Pseudomonas hibiscicola* (ATCC 19867); *Pseudomonas huttiensis* (ATCC 14670); *Pseudomonas hydrogenovora; Pseudomonas jessenii* (ATCC 700870); *Pseudomonas kilonensis; Pseudomonas lanceolata* (ATCC 14669); *Pseudomonas lini; Pseudomonas marginata* (ATCC 25417); *Pseudomonas mephitica* (ATCC 33665); *Pseudomonas denitrificans* (ATCC 19244); *Pseudomonas pertucinogena* (ATCC 190); *Pseudomonas pictorum* (ATCC 23328); *Pseudomonas psychrophila; Pseudomonas filva* (ATCC 31418); *Pseudomonas monteilii* (ATCC 700476); *Pseudomonas mosselii; Pseudomonas oryzihabitans* (ATCC 43272); *Pseudomonas plecoglossicida* (ATCC 700383); *Pseudomonas putida* (ATCC 12633); *Pseudomonas reactans; Pseudomonas spinosa* (ATCC 14606); *Pseudomonas balearica; Pseudomonas luteola* (ATCC 43273); *Pseudomonas stutzeri* (ATCC 17588); *Pseudomonas amygdali* (ATCC 33614); *Pseudomonas avellanae* (ATCC 700331); *Pseudomonas caricapapayae* (ATCC 33615); *Pseudomonas cichorii* (ATCC 10857); *Pseudomonas ficuserectae* (ATCC 35104); *Pseudomonas fuscovaginae; Pseudomonas meliae* (ATCC 33050); *Pseudomonas syringae* (ATCC 19310); *Pseudomonas viridiflava* (ATCC 13223); *Pseudomonas thermocarboxydovorans* (ATCC 35961); *Pseudomonas thermotolerans; Pseudomonas thivervalensis; Pseudomonas vancouverensis* (ATCC 700688); *Pseudomonas wisconsinensis*; and *Pseudomonas xiamenensis*.

The host cell can also be selected from "Gram-negative Proteobacteria Subgroup 17." "Gram-negative Proteobacteria Subgroup 17" is defined as the group of Proteobacteria known in the art as the "fluorescent Pseudomonads" including those belonging, e.g., to the following *Pseudomonas* species: *Pseudomonas azotoformans; Pseudomonas brenneri; Pseudomonas cedrella; Pseudomonas corrugata; Pseudomonas extremorientalis; Pseudomonas fluorescens; Pseudomonas gessardii; Pseudomonas libanensis; Pseudomonas mandelii; Pseudomonas marginalis; Pseudomonas migulae; Pseudomonas mucidolens; Pseudomonas orientalis; Pseudomonas rhodesiae; Pseudomonas synxantha; Pseudomonas tolaasii*; and *Pseudomonas veronii*.

Codon Optimization

Methods for optimizing codons to improve expression in bacterial hosts are known in the art and described in the literature. For example, optimization of codons for expression in a *Pseudomonas* host strain is described, e.g., in U.S. Pat. App. Pub. No. 2007/0292918, "Codon Optimization Method," incorporated herein by reference in its entirety.

Codon optimization for expression in *E. coli* is described, e.g., by Welch, et al., 2009, PLoS One, "Design Parameters to Control Synthetic Gene Expression in *Escherichia coli*, 4(9): e7002, Ghane, et al., 2008, "Overexpression of Biologically Active Interferon B Using Synthetic Gene in *E. coli*," Journal of Sciences, Islamic Republic of Iran 19(3): 203-209, and Valente, et al., 2004, "Translational Features of Human Alpha 2b Interferon Production in *Escherichia coli*," Applied and Environmental Microbiology 70(8): 5033-5036, all incorporated by reference herein.

Fermentation Format

The expression system according to the present invention can be cultured in any fermentation format. For example, batch, fed-batch, semi-continuous, and continuous fermentation modes may be employed herein.

In embodiments, the fermentation medium may be selected from among rich media, minimal media, and mineral salts media. In other embodiments either a minimal medium or a mineral salts medium is selected. In certain embodiments, a mineral salts medium is selected.

Mineral salts media consists of mineral salts and a carbon source such as, e.g., glucose, sucrose, or glycerol. Examples of mineral salts media include, e.g., M9 medium, *Pseudomonas* medium (ATCC 179), and Davis and Mingioli medium (see, B D Davis & E S Mingioli (1950) J. Bact. 60:17-28). The mineral salts used to make mineral salts media include those selected from among, e.g., potassium phosphates, ammonium sulfate or chloride, magnesium sulfate or chloride, and trace minerals such as calcium chloride, borate, and sulfates of iron, copper, manganese, and zinc. Typically, no organic nitrogen source, such as peptone, tryptone, amino acids, or a yeast extract, is included in a mineral salts medium. Instead, an inorganic nitrogen source is used and this may be selected from among, e.g., ammonium salts, aqueous ammonia, and gaseous ammonia. A mineral salts medium will typically contain glucose or glycerol as the carbon source. In comparison to mineral salts media, minimal media can also contain mineral salts and a carbon source, but can be supplemented with, e.g., low levels of amino acids, vitamins, peptones, or other ingredients, though these are added at very minimal levels. Media can be prepared using the methods described in the art, e.g., in U.S. Pat. App. Pub. No. 2006/0040352, referenced and incorporated by reference above. Details of cultivation procedures and mineral salts media useful in the methods of the present invention are described by Riesenberg, D et al., 1991, "High cell density cultivation of *Escherichia coli* at controlled specific growth rate," J. Biotechnol. 20 (1):17-27.

Fermentation may be performed at any scale. The expression systems according to the present invention are useful for recombinant protein expression at any scale. Thus, e.g., microliter-scale, centiliter scale, and deciliter scale fermentation volumes may be used, and 1 Liter scale and larger fermentation volumes can be used.

In embodiments, the fermentation volume is at or above about 1 Liter. In embodiments, the fermentation volume is about 1 liter to about 100 liters. In embodiments, the fermentation volume is about 1 liter, about 2 liters, about 3 liters, about 4 liters, about 5 liters, about 6 liters, about 7 liters, about 8 liters, about 9 liters, or about 10 liters. In embodiments, the fermentation volume is about 1 liter to about 5 liters, about 1 liter to about 10 liters, about 1 liter to about 25 liters, about 1 liter to about 50 liters, about 1 liter to about 75 liters, about 10 liters to about 25 liters, about 25 liters to about 50 liters, or about 50 liters to about 100 liters In other embodiments, the fermentation volume is at or above 5 Liters, 10 Liters, 15 Liters, 20 Liters, 25 Liters, 50 Liters, 75 Liters, 100 Liters, 200 Liters, 500 Liters, 1,000 Liters, 2,000 Liters, 5,000 Liters, 10,000 Liters, or 50,000 Liters.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

EXAMPLES

Example 1

Production of rIFN-β from High Throughput Expression Samples

In the following experiment, IFN-β C17S expression strains were constructed, and the amount of IFN-β in the insoluble fraction obtained for each was quantitated. Based on the resulting data, certain strains were selected for use in optimizing the non-denaturing extraction process of the present invention.

Construction and Growth of IFN-β Expression Strains

The IFN-β 1b coding sequence was constructed using *P. fluorescens* preferred codons to encode for the human IFN-β amino acid sequence corresponding to the therapeutic Betaseron. FIG. 7 shows the amino acid (SEQ ID NO: 1) and DNA sequences (SEQ ID NO: 2) of the synthetic IFN-β (Betaseron) gene.

Plasmids were constructed which carry the codon-optimized IFN-β fused to nineteen *P. fluorescens* secretion leaders. The secretion leaders were included to target the protein to the periplasm where it may be recovered in the properly folded and active form. In addition, one plasmid was constructed which carries the codon-optimized IFN-β designed for cytoplasmic expression.

Expression of IFN-β was driven from the Ptac promoter and translation initiated from either a high (Hi) or medium (Med) activity ribosome binding site (RBS). The resulting 20 plasmids were transformed into 30 *P. fluorescens* host strains (16 protease deletion strains, 13 folding modulator overexpression strains and 1 wild type strain) to produce 600 expression strains (see Tables 6 and 7). Folding modulators, when present, were encoded on a second plasmid and expression driven by a mannitol inducible promoter.

The thirty host strains carrying each of 20 IFN-β expression plasmids (600 expression hosts in total) were grown in triplicate in 96-well plates. Samples harvested 24 hours after induction were used for analysis.

Expression of IFN-β Using Pfēnex Expression Technology in 96-Well Format

Each plasmid (Table 6) was transformed into 30 *P. fluorescens* host strains (Table 7) as follows: Twenty-five microliters of competent cells were thawed and transferred into a 96-well electroporation plate (BTX ECM630 Electroporator), and 1 microliter miniprep plasmid DNA was added to each well. Cells were electroporated at 2.5 KV, 200 Ohms, and 25 µF. Cells were resuspended in 75 microliters HTP-YE media with trace minerals, transferred to 96-well deep well plate with 500 µl M9 salts 1% glucose medium (seed culture), and incubated at 30° C., shaking 300 rpm and 50-mm diameter throw for 48 hours.

Ten microliters of seed culture were transferred into triplicate wells of 96-well deep well plates, each well containing 500 microliters of HTP-YE medium, and incubated as before for 24 hours. Isopropyl-β-D-1-thiogalactopyranoside (IPTG) was added to each well for a final concentration of 0.3 mM to induce the expression of IFN-β. For growth of small cultures in HTP microwells, a specific culture pH is not tightly controlled and the cell density can differ slightly from well to well. Mannitol (Sigma, M1902) was added to each well at a final concentration of 1% to induce the expression of folding modulators in folding modulator over-expressing strains, and the temperature was reduced to 25° C. Twenty four hours after induction, cultures were collected for analysis. For OD normalization, cells were mixed with sterile 1×PBS to obtain a final OD600=20 in a final volume of 400 microliters using the Biomek liquid handling station (Beckman Coulter). Samples were collected in cluster tube racks.

Sample Preparation and SDS-CGE Analysis

Soluble fractions (supernatants obtained after centrifugation of lysates) and insoluble fractions (pellets obtained after centrifugation of lysates) were prepared by sonicating the OD-normalized cultures, followed by centrifugation. Frozen, normalized culture broth (400 microliters) was thawed and sonicated for 3.5 minutes. The lysates were centrifuged at 20,800×g for 20 minutes (4° C.) and the soluble fractions removed using manual or automated liquid handling. The insoluble fractions were frozen and then thawed for re-centrifugation at 20,080×g for 20 minutes at 4° C., to remove residual supernatant. The insoluble fractions were then resuspended in 400 µL of 1× phosphate buffered saline (PBS), pH 7.4. Further dilutions of soluble and insoluble fractions for SDS-CGE analysis were performed in 1× phosphate buffered saline (PBS), pH 7.4. Soluble and insoluble fractions were prepared for analysis by SDS capillary gel electrophoresis (CGE) (Caliper Life Sciences, Protein Express LabChip Kit, Part 760301), in the presence of dithiothreitol (DTT).

Normalized soluble and insoluble fractions from each well of the 600 strains expressing IFN-β were analyzed by reducing SDS-CGE analysis in one replicate for the soluble fractions and insoluble fractions. No IFN-β signal was detected in the soluble fractions. IFN-β signal varied from no signal to greater than 400 mg/L in the insoluble fractions. Only five of the twenty plasmids tested showed measurable signal of IFN-β in the insoluble fractions of all thirty host strains: p530-001, p530-007, p530-011, p530-018 and p530-020. Valley to valley integration of IFN-β signal using Caliper LabChipGX software was performed in all 150 strains consisting of the five plasmids listed above in the thirty host strains, and data were used to calculate volumetric yields. Volumetric yields of the 150 strains analyzed ranged from 2 to 482 mg/L. Strains carrying p530-020 attained consistently higher yields of IFN-β in the insoluble fraction than other expression strains; however, the protein migrated higher than expected on SDS-CGE, indicating that the secretion leader was not cleaved. High yields were also observed with 2 host strains carrying p530-001. No significant difference in IFN-β in the insoluble fraction was observed among the 30 strains except potentially in one strain, DC441, a lon hslUV protease deletion strain, which showed somewhat higher yields than the other 29 strains.

A subset of 17 top expression strains (Table 8), excluding strains containing plasmid p530-020, was selected for further analyses. The expression strains containing plasmid p530-020 were excluded from further consideration in this experiment due to the potentially unprocessed leader. SDS-CGE analysis was performed on the soluble and insoluble fractions for these strains. Quantification of the SDS-CGE output is shown in Table 8. IFN-β protein concentration ranged from 102 to greater than 482 mg/L. Based upon insoluble yield and processing of either the periplasmic leader sequence or the N-terminal Met from IFN-β, strains were chosen to proceed to fermentation assessment.

TABLE 6

Plasmids

| Plasmid | Expression Vector | Secretion Leader | RBS |
|---|---|---|---|
| p530-001 | pDOW5271 | None | Hi |
| p530-002 | pDOW5204 | Pbp | Med |
| p530-003 | pDOW5206 | DsbA | Hi |
| p530-004 | pDOW5207 | DsbA | Med |
| p530-005 | pDOW5209 | Azu | Hi |
| p530-006 | pDOW5210 | Azu | Med |
| p530-007 | pDOW5217 | LAO | Hi |
| p530-008 | pDOW5220 | Ibp-S31A | Hi |
| p530-009 | pDOW5223 | TolB | Hi |
| p530-010 | pDOW5226 | Trc | Hi |
| p530-011 | pDOW5232 | Ttg2C | Hi |
| p530-012 | pDOW5235 | FlgI | Hi |
| p530-013 | pDOW5238 | CupC2 | Hi |
| p530-014 | pDOW5241 | CupB2 | Hi |
| p530-015 | pDOW5244 | CupA2 | Hi |
| p530-016 | pDOW5247 | NikA | Hi |
| p530-017 | pDOW5256 | PorE | Hi |
| p530-018 | pDOW5259 | Pbp-A20V | Hi |
| p530-019 | pDOW5262 | DsbC | Hi |
| p530-020 | pDOW5265 | Bce | Hi |

TABLE 7

IFN-β Expression Strains

| Strain Name | Strain Description |
|---|---|
| DC454 | Wild type |
| DC441 | PD |
| DC462 | FMO |
| DC468 | PD |
| DC469 | PD |
| DC485 | PD |
| DC486 | PD |
| DC487 | PD |
| DC488 | PD |
| DC489 | PD |
| DC490 | PD |
| DC491 | PD |
| DC492 | PD |
| DC498 | PD |
| DC538 | FMO |
| DC539 | FMO |
| DC544 | FMO |
| DC547 | FMO |
| DC548 | FMO |
| DC552 | FMO |
| DC565 | FMO |
| DC566 | FMO |
| DC567 | FMO |
| DC568 | FMO |
| DC575 | FMO |
| DC584 | FMO |
| DC598 | FMO |
| DC599 | FMO |
| DC667 | FMO |
| DC954 | PD |

PD = protease deletion strain, FMO = folding modulator over-expression strain

TABLE 8

Calculated Volumetric IFN-β Yields of Top 17 Strains by SDS-CGE

| Strain Name | Vol. Yield >100 ug/ml | Plasmid | Host Strain | Leader |
|---|---|---|---|---|
| PS530-001 | 482.3 | p530-001 | DC441 | x |
| PS530-101 | 216.5 | p530-001 | DC485 | x |
| PS530-011 | 161.1 | p530-011 | DC441 | ttg2C |

TABLE 8-continued

Calculated Volumetric IFN-β
Yields of Top 17 Strains by SDS-CGE

| Strain Name | Vol. Yield >100 ug/ml | Plasmid | Host Strain | Leader |
|---|---|---|---|---|
| PS530-071 | 148.8 | p530-011 | DC468 | ttg2C |
| PS530-007 | 141.2 | p530-007 | DC441 | Lao |
| PS530-031 | 131.3 | p530-011 | DC454 | ttg2C |
| PS530-201 | 122.6 | p530-001 | DC490 | x |
| PS530-531 | 121.0 | p530-011 | DC598 | ttg2C |
| PS530-211 | 119.8 | p530-011 | DC490 | ttg2C |
| PS530-151 | 119.8 | p530-011 | DC487 | ttg2C |
| PS530-061 | 119.6 | p530-001 | DC468 | x |
| PS530-411 | 114.0 | p530-011 | DC565 | ttg2C |
| PS530-231 | 113.3 | p530-011 | DC491 | ttg2C |
| PS530-391 | 112.2 | p530-011 | DC552 | ttg2C |
| PS530-027 | 104.5 | p530-007 | DC454 | Lao |
| PS530-291 | 103.3 | p530-011 | DC538 | ttg2C |
| PS530-271 | 102.2 | p530-011 | DC498 | ttg2C |

Example 2

Extraction of IFN-β 1b from High Throughput Expression Material

IFN-β 1b was successfully extracted from insoluble fractions from HTP expression cultures, using extraction conditions comprising Zwittergent 3-14 detergent.

Figure 1:
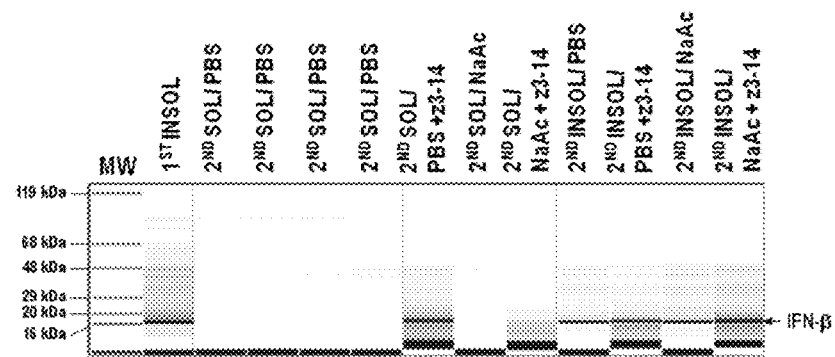
FIGS. 1A and 1B. Initial CGE evaluation of IFN-β recovered from *P. fluorescens* strain PS530-001. 1A. Protein analyzed under reducing conditions. 1B. Protein analyzed under nonreducing conditions.
Figure 1:
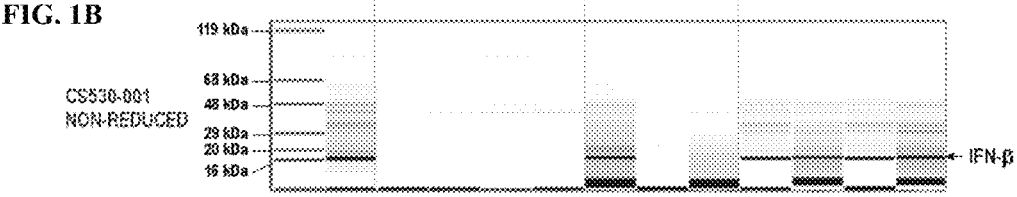

HTP expression plate cultures of *Pseudomonas fluorescens* strains PS530-001 overexpressing cytoplasmic IFN-β 1b and 530-220, overexpressing secreted IFN-β 1b (described in Example 1), were sonicated and centrifuged to obtain an insoluble fraction and a soluble fraction. The pellets were resuspended in extraction buffer 1×PBS, pH 7.4 or sodium acetate at pH 4.5. Each buffer was tested either with or without Zwittergent 3-14 detergent at 1% (w/v). Each of the four combinations of buffer and detergent was incubated for 1-2 hours at room temperature or overnight at 4° C. with shaking. After extraction, each sample was centrifuged for 20 minutes at 20,080×g at 4° C. to produce a second insoluble pellet fraction (extract pellet) and a second soluble supernatant fraction (extract supernatant). The first insoluble fraction and first soluble fraction, and the extract pellet fraction and extract supernatant fraction, were analyzed by SDS-CGE. The results are shown in FIGS. 1A and 1B. As seen in Lane 7, the extraction condition including PBS buffer and Zwittergent 3-14 yielded soluble IFN-l3.

Example 3

Optimization of Conditions for Extraction

Insoluble fractions from fermentation cultures were extracted under conditions comprising different detergents.

Frozen cell paste from a 1 L fermentation (grown at 32° C., pH 6.5, and induced using 0.2 mM IPTG at an $OD_{575}$ of 100) of strain PS530-001, overexpressing recombinant IFN-β 1b, was resuspended in lysis buffer containing 20 mM sodium phosphate (JT Baker), pH 7.4 to a final solids concentration of 20% (w/v). The well-mixed cell slurry was lysed with two passes at 38 kpsi through a Constant cell disruptor (Constant Systems, Inc.). The lysate was split in half, and spun by centrifugation at 15,000×g for 30 minutes at 4° C. (Beckman Coulter, PN# J-20, XPF). The pellets (containing IFN-β and cell debris) were resuspended and each was washed in either Buffer A (20 mM sodium phosphate, pH 7.4) or Buffer B (20 mM sodium acetate, pH 4.0). Samples were spun by centrifugation under the same conditions described for the first spin, supernatants were removed, and the pellets were again resuspended in either Buffer A or B at 20% solid concentration. For each buffer, twenty aliquots of 1 mL each were placed in 1.5 mL conical tubes. Detergent stock solutions were added to the conical tubes at different concentrations. All tubes were incubated at room temperature for 1 hour or overnight (18 hours) at 4° C. with continuous mixing. After extraction, the solutions were centrifuged and the extract supernatant fractions were analyzed for protein concentration by SDS-CGE. FIG. 2 provides a flow chart showing how the sample preparation and extraction were carried out.

Of the detergents tested, Zwittergent 3-14 and N-lauroylsarcosine (NLS), were found to give the best yields regardless of buffer and incubation time (Table 9). However, the product extracted using NLS was not active, as determined by its inability to bind to either a Blue Sepharose affinity column or a cation exchange column (SP HP) (data not shown). The product extracted using Zwittergent 3-14 was determined to be active.

TABLE 9

Evaluation of Detergents for Extraction

| Detergent | Detergent Concentration (w/v) | Extracted Product Concentration (ug/mL) | | | |
|---|---|---|---|---|---|
| | | Buffer A | | Buffer B | |
| | | 1 hr @RT | 18 hr @RT | 1 hr @RT | 18 hr @RT |
| Zwittergent 3-14 | 0.50% | 748 | 557 | 1011 | 734 |
| | 1.00% | 731 | 392 | 1060 | 936 |
| | 2.00% | 903 | 398 | 1548 | 1146 |
| Lauroylsarcosine | 0.20% | 1023 | 643 | NA | NA |
| | 0.50% | 3104 | 2125 | 324 | 150 |
| | 1.50% | 2782 | 2670 | 2319 | 2668 |
| NDSB195 | 10.00% | 8 | 6 | 11 | 46 |
| | 15.00% | 14 | 13 | 31 | 119 |
| NDSB256 | 5.00% | 20 | 56 | 15 | 43 |
| | 15.00% | 204 | 233 | 114 | 135 |
| Chaps | 0.50% | 11 | 36 | 98 | 160 |
| | 2.00% | 75 | 170 | 179 | 250 |
| Octylglucopyranoside | 1.00% | 83 | 175 | 121 | 169 |
| | 5.00% | 196 | 258 | 164 | 215 |
| Sodium | 0.50% | 129 | 237 | NA | NA |

TABLE 9-continued

Evaluation of Detergents for Extraction

| Detergent | Detergent Concentration (w/v) | Extracted Product Concentration (ug/mL) | | | |
|---|---|---|---|---|---|
| | | Buffer A | | Buffer B | |
| | | 1 hr @RT | 18 hr @RT | 1 hr @RT | 18 hr @RT |
| Deoxycholate | 1.00% | 196 | 274 | NA | NA |
| Tween-20 | 0.05% | 4 | 11 | NA | 6 |
| | 0.50% | 11 | 37 | 3 | 18 |
| Tween-80 | 0.01% | 4 | 6 | NA | 7 |
| | 0.10% | 5 | 10 | NA | 12 |
| | 0.50% | 7 | 25 | 3 | 21 |
| Triton-100 | 0.10% | 25 | 68 | 33 | 103 |
| | 1.00% | 40 | 85 | 62 | 176 |

Evaluation of Zwittergent Analogs

Using similar methods, Zwittergent analogs were evaluated for their extraction efficiency. The results are shown in Table 10. The best yields were observed with Zwittergent 3-14. Zwittergent 3-12, Zwittergent 3-10, and Zwittergent 3-08 were also effective.

TABLE 10

Evaluation of Zwittergent Analogs for Extraction of IFN-β 1b

| Detergent | Detergent Conc. | Solid Conc. | Protein (ug/mL) |
|---|---|---|---|
| Zwittergent 3-08 | 10% | 20% | 292 |
| Zwittergent 3-10 | 1.0% | 20% | 233 |
| Zwittergent 3-12 | 1.0% | 20% | 357 |
| Zwittergent 3-16 | 0.1% | 20% | 17 |
| Zwittergent 3-14 | 1.0% | 20% | 430 |
| Zwittergent 3-14 | 1.0% | 10% | 396 |
| Zwittergent 3-14 | 1.0% | 5% | 548 |

Evaluation of the Zwittergent 3-14 Concentration

To efficiently solubilize proteins, the detergent concentration typically needs to be above its CMC value. The CMC of Zwittergent 3-14 is about 0.01% w/v. Extraction conditions including sodium phosphate buffer at pH 7.4 with increasing concentrations of Zwittergent 3-14 were evaluated. The cell paste used was obtained by growing strain PS530-001 at 32° C., pH 6.5, and induced using 0.2 mM IPTG at an $OD_{575}$ of 100. The results in Table 11 show that use of Zwittergent 3-14 at 1% (w/v) concentration resulted in the highest extraction yield.

TABLE 11

Effect of Zwittergent 3-14 Concentration on Extraction of IFN-β 1b

| Zwittergent 3-14 Concentration (% w/v) | Extraction Yield microgram/mL | Extraction Yield % IFN-β protein extracted from insoluble pellet (insoluble fraction) |
|---|---|---|
| 0.01% | 10 | 0% |
| 0.05% | 36 | 1% |
| 0.10% | 72 | 2% |
| 0.50% | 341 | 9% |
| 1.00% | 787 | 21% |
| 2.00% | 620 | 17% |

Evaluation of Additional Chemical Reagents

As shown in Table 11, extraction conditions including Zwittergent 3-14 at 1% (w/v) concentration in sodium phosphate buffer at pH 7.4 yielded 21% of the IFN-β 1b detected in the original insoluble fraction. Further optimization was conducted.

High concentration (e.g., 6 to 8 M) of some chaotropic reagents like urea and guanidinium hydrochloride commonly have been used as a strong denaturant for solubilization of inclusion bodies. Chaotropes such as urea can increase the detergent critical micelle concentration (CMC) and may potentially improve the extraction efficiency. Low concentrations of urea (up to 2 M) were evaluated in the extraction conditions. Salts, e.g., NaCl, can also affect detergent CMC. Varying Zwittergent 3-14 concentrations were evaluated due to the potential interplay between detergent CMC and the presence of chaotropic reagents and salts. The concentration of insoluble inclusion solids in the extraction conditions was also varied. Lower solids concentration than the 20% (w/v) previously used were evaluated.

In summary, the effect of varying the following parameters on extraction efficiency was tested.

Sodium Chloride: 150-1850 mM
Urea: 0-2 M
Zwittergent 3-14: 0.1-1.0% w/v
Solids: 5-20% w/v
pH: 6.5-8.5

The flow chart in FIG. 3 describes the preparation and extraction of the first insoluble pellet fraction for this optimization study. Table 12 shows the result of the study. FIGS. 4A and B summarize the results and significance of the effect of each parameter on the extraction yield. For optimization of extraction of interferon β from the insoluble fraction, a two-level five-factor half-fractional factorial experimental design was used. JMP software (SAS Institute, Cary, N.C.) was used for experimental design and analysis. The software estimates the effect of individual factors as well as interactions on experimental output (amount of interferon extracted).

TABLE 12

Results of Extraction Study

| No. | | Solids (%) | pH | NaCl (M) | Urea (M) | Z314 (%) | Interferon-β in extract supernatant (mg/L) |
|---|---|---|---|---|---|---|---|
| 1 | ----+ | 5 | 6.5 | 0.15 | 0 | 1 | 2275 |
| 2 | ---+- | 5 | 6.5 | 0.15 | 2 | 0.1 | 896 |
| 3 | --+-- | 5 | 6.5 | 1.85 | 0 | 0.1 | 246 |
| 4 | --+++ | 5 | 6.5 | 1.85 | 2 | 1 | 7024 |
| 5 | -+--- | 5 | 8.5 | 0.15 | 0 | 0.1 | 638 |

TABLE 12-continued

Results of Extraction Study

| No. | | Solids (%) | pH | NaCl (M) | Urea (M) | Z314 (%) | Interferon-β in extract supernatant (mg/L) |
|---|---|---|---|---|---|---|---|
| 6  | −+−++  | 5    | 8.5 | 0.15 | 2 | 1    | 5614 |
| 7  | −++−+  | 5    | 8.5 | 1.85 | 0 | 1    | 5414 |
| 8  | −+++−  | 5    | 8.5 | 1.85 | 2 | 0.1  | 1711 |
| 9  | 0      | 12.5 | 7.5 | 1    | 1 | 0.55 | 3362 |
| 10 | 0      | 12.5 | 7.5 | 1    | 1 | 0.55 | 3693 |
| 11 | 0      | 12.5 | 7.5 | 1    | 1 | 0.55 | 3809 |
| 12 | +−−−−  | 20   | 6.5 | 0.15 | 0 | 0.1  | 65   |
| 13 | +−−++  | 20   | 6.5 | 0.15 | 2 | 1    | 2345 |
| 14 | +−+−+  | 20   | 6.5 | 1.85 | 0 | 1    | 2149 |
| 15 | +−++−  | 20   | 6.5 | 1.85 | 2 | 0.1  | 438  |
| 16 | ++−−+  | 20   | 8.5 | 0.15 | 0 | 1    | 2350 |
| 17 | ++−+−  | 20   | 8.5 | 0.15 | 2 | 0.1  | 677  |
| 18 | +++−−  | 20   | 8.5 | 1.85 | 0 | 0.1  | 199  |
| 19 | +++++  | 20   | 8.5 | 1.85 | 2 | 1    | 4486 |

Based on the above data, an optimized extraction condition was selected for experiments described hereinafter: 1% (w/v) Zwittergent 3-14, 2 M Urea, 2 M NaCl, Solids 5% w/v, buffer pH 7.5 to 8.5. Using these optimized conditions, the observed extraction yield (in the extract supernatant) was found to be consistently 90% or above (i.e., 90% or more of the amount of recombinant protein measured in the insoluble fraction).

Example 4

Production of rIFN-β 1b from Large Scale Fermentation

Production of recombinant human-β interferon (IFN-β 1b) protein in *Pseudomonas fluorescens* Pfēnex Expression Technology™ strain PS530-001 was successfully achieved in 2 liter fermentors. Multiple fermentation conditions were evaluated resulting in expression of IFN-β 1b up to 9.2 g/L.

Fermentation cultures were grown in 2 liter fermentors containing a mineral salts medium (as described herein and also by, e.g., Riesenberg, D., et al., 1991). Culture conditions were maintained at 32° C. and pH 6.5 through the addition of aqueous ammonia. Dissolved oxygen was maintained in excess through increases in agitation and flow of sparged air and oxygen into the fermentor. Glycerol was delivered to the culture throughout the fermentation to maintain excess levels. These conditions were maintained until the target culture optical density (A575) for induction was reached, at which time IPTG was added to initiate IFN-β production. The optical density at induction, the concentration of IPTG, pH and temperature were all varied to determine optimal conditions for expression. After 24 hours, the culture from each fermentor was harvested by centrifugation and the cell pellet frozen at −80° C.

Fermentation cultures were induced at 100 $OD_{575}$ using 0.2 mM IPTG, at pH 6.5 and a temperature of 32° C. Replicate fermentations resulted in IFN-β production at 7.5, 8.4 and 7.9 g/L as determined by SDS-CGE of the initial insoluble fraction (FIG. 5). When these insoluble fractions were subjected to extraction (under conditions including 1% (w/v) Zwittergent 3-14, 2 M Urea, 2 M NaCl, Solids 5% w/v, and buffer pH 8.2), solubilized IFN-β were observed in the extract supernatant at 2.2, 2.4, and 2.6 g/L. This represents an average extraction yield of 31%.

Increasing the induction OD to 120 to 160, and decreasing the fermentation pH to 5.7 to 6.25, increased IFN-β titers in the initial insoluble fraction to 8.8-9.2 g/L (FIG. 6). Extraction of these cell pellets (using the same extraction conditions as for the experiment shown in FIG. 5) resulted in 3.1 to 4.0 g/L of IFN-β in the extracted supernatant fraction, an average extraction yield of 39% (Table 13).

TABLE 13

Extracted Solubilized IFN-β Based on Induction Conditions

| | Induction OD of 100 and pH 6.5 | | | | Induction OD of 120-160 and pH 5.7 to 6.25 | | |
|---|---|---|---|---|---|---|---|
| | Total Insoluble Titer (g/L) | Extracted Solubilized Titer (g/L) | Extracted Yield (%) | | Total Insoluble Titer (g/L) | Extracted Solubilized Titer (g/L) | Extracted Yield (%) |
| u2      | 7.5 | 2.2 | 29  | u2      | 9.2 | 4.0 | 43  |
| u7      | 8.4 | 2.4 | 29  | u3      | 8.8 | 3.1 | 35  |
| u8      | 7.9 | 2.6 | 33  | u5      | 8.8 | ND  | ND  |
| average | 7.9 | 2.4 | 31  | average | 8.9 | 3.5 | 39  |
| std dev | 0.4 | 0.2 | 2.3 | std dev | 0.3 | 0.6 | 5.6 |

Example 5

Activity Analysis of IFN-β Extraction Product

Broth from fermentation of *Pseudomonas fluorescens* strain PS530-001 (1 L fermentation at 32° C., pH 6.0, induced at $OD_{575}$ of 100 using 0.2 mM IPTG) was centrifuged and the supernatant discarded. The cell paste was resuspended in 20 mM Tris, pH 8.2 (in a ratio of 1:4) and lysed by passing through Microfluidics Microfluidizer M110Y at 15,000 psi. The lysate was centrifuged and the soluble fraction discarded. The insoluble fraction was mixed with extraction buffer (20 mM Tris, 2 M NaCl, 2 M urea, 1% Zwittergent 3-14, pH 8.2) at room temperature for 1 hour and centrifuged to produce an extract supernatant fraction and an extract pellet fraction. The extraction yield of IFN-β (IFN-β in extract supernatant fraction/IFN-β in the initial insoluble fraction) was close to 100% (>99%) based on SDS-CGE analysis (data not shown).

The extract supernatant was filtered and loaded on a 5 mL GE Healthcare Blue Sepharose column equilibrated with 20 mM Tris, 2 M NaCl, pH 8.2. The column was washed with the same buffer and the IFN-β eluted with 20 mM Tris, 2 M NaCl, 50% propylene glycol, pH 8.2. The protein in the elution pool was analyzed by SDS-CGE and found to be more than 98% pure IFN-β. Aliquots of the elution pool were exchanged into Buffers C (5 mM glycine pH 3.0) and D (5 mM aspartic acid, 9% trehalose, pH 4.0).

The exchanged samples were analyzed by SDS-CGE as well as with a cell-based assay (PBL Interferon Source, #51100-1). The cell-based assay uses a human cell line (PIL5) sensitized with IFN-type 1 receptor. IFN-β binds to the receptor, which sends a signal via the Jak1/STAT1 signal transduction pathway, activating ISG15-luciferase transcription via the Interferon Sensitive Response Element (ISRE). Cell-based assay kit instructions were followed as per manufacturer's protocol (51100 rev01). The signal was read using conventional plate readers with luminescence detection. Table 14 summarizes the SDS-CGE and cell-based assay results, which indicate that the IFN-β in the samples was fully active.

TABLE 14

Results of Activity Assays

| Sample | SDS-CGE (mg/L) | Cell-based assay (mg/L) |
|---|---|---|
| Blue-Sepharose Elution pool in Exchange Buffer A | 436 | 477 |
| Blue-Sepharose Elution pool in Exchange Buffer B | 404 | 404 |

Example 6

Production of IFN-α 2a and 2b from High Throughput Expression Samples

IFN-α 2a and IFN-α 2b coding sequences were constructed using *P. fluorescens* preferred codons to encode for the human proteins. FIG. 8 shows the amino acid (SEQ ID NO: 4) and DNA sequences (SEQ ID NO: 5) of the synthetic IFN-α 2a gene, and FIG. 9 shows the amino acid (SEQ ID NO: 6) and DNA sequences of the synthetic IFN-α 2b gene (SEQ ID NO: 7).

Plasmids expressing either protein were constructed and transformed into different host strains. Expression strains were tested for their ability to express recombinant protein using HTP analysis, as described with regard to IFN-β herein. A subset of the expression strains are selected for fermentation studies.

The selected strains were grown and induced according to the present invention. The cells were centrifuged, lysed, and centrifuged again as described herein for IFN-β. The resulting insoluble fraction and first soluble fraction were extracted using extraction conditions described herein. The resulting IFN-α 2a and IFN-α 2b extract supernatants were quantitated using SDS-CGE (data not shown).

Example 7

Extraction of IFN-α 2a and 2b from High Throughput Expression Material

The first insoluble fraction obtained as described in Example 6 is extracted using the extraction conditions of the present invention. IFN-α 2a and 2b in the resulting second soluble fractions are evaluated by CGE and bioactivity assay.

Example 8

Production of IFN-α 2a and 2b from Large Scale Fermentation

IFN-α 2a and 2b expressing strains selected by HTP analysis are grown in 2 liter fermentors using optimized fermentation conditions of the present invention, e.g., as described in Example 4. The first insoluble fraction is extracted using the methods of the present invention, e.g., as described in Example 4. The IFN-α 2a and 2b protein present in the first insoluble and second soluble fractions are evaluated by CGE and compared.

Example 9

Analysis of IFN-α 2a and 2b Extraction Product

The extraction product obtained in Example 8 is analyzed for IFN-α 2a and 2b bioactivity.

What is claimed is:

1. A method for producing a recombinant Type 1 interferon protein, said method comprising:
   expressing the recombinant Type I interferon protein by culturing a *Pseudomonas* or *E. coli* host cell containing an expression construct comprising a nucleotide sequence encoding the recombinant Type I interferon protein that has been optimized for expression in the host cell, wherein the recombinant Type I interferon protein is expressed in the cytoplasm of the host cell;
   lysing the cultured host cell;
   obtaining an insoluble fraction and a soluble fraction from the lysed host cell;
   extracting the insoluble fraction by subjecting it to non-denaturing extraction conditions;
   wherein the non-denaturing extraction conditions comprise a Zwitterionic detergent at a concentration of about 0.5% to about 2%, to obtain soluble recombinant Type 1 interferon protein without the use of a renaturing or refolding step;
   separating the obtained soluble recombinant Type 1 interferon protein from other protein and cellular debris; and
   measuring the activity of the separated soluble recombinant Type 1 interferon protein, wherein about 80% to about 100% of the separated soluble recombinant Type 1 interferon protein is determined to be active.

2. The method of claim 1, wherein the Zwitterionic detergent is n-Octyl-N,N-dimethyl-3-ammonio-1-propane-sulfonate, n-Decyl-N,N-dimethyl-3-ammonio-1-propane-sulfonate, n-dodecyl-N,N-dimethyl-3-ammonio-1-propane-sulfonate, or n-Tetradecyl-N,N-dimethyl-3-ammonio-1-propane sulfonate.

3. The method of claim 2, wherein the non-denaturing extraction conditions comprise about 0.5% to about 2% n-Tetradecyl-N,N-dimethyl-3-ammonio-1-propane sulfonate.

4. The method of claim 1, wherein the non-denaturing extraction conditions further comprise a chaotropic agent and a cosmotropic salt.

5. The method of claim 4, wherein the chaotropic agent is urea or guanidinium hydrochloride, and wherein the cosmotropic salt is NaCl, KCl, or $(NH_4)_2SO_4$.

6. The method of claim 5, wherein the non-denaturing extraction conditions comprise: about 0.5 to about 2% n-Tetradecyl-N,N-dimethyl-3-ammonio-1-propane sulfonate; about 0 to about 2 M urea; about 0 to about 2 M NaCl; and wherein the pH is about 6.5 to about 8.5.

7. The method of claim 6, wherein the non-denaturing extraction conditions comprise: about 2% n-Tetradecyl-N,N-dimethyl-3-ammonio-1-propane sulfonate; about 2 M urea; about 2 M NaCl; and wherein the pH is about 8.0.

8. The method of claim 7, wherein the non-denaturing extraction conditions additionally comprise about 5% w/v solids.

9. The method of claim 6, wherein the non-denaturing extraction conditions additionally comprise about 1% to about 40% w/v solids.

10. The method of claim 1, wherein the recombinant Type 1 interferon protein is an interferon-β, an interferon-α, an interferon-κ, or an interferon-ω.

11. The method of claim 10, wherein the recombinant Type 1 interferon protein is an interferon-β, and wherein said interferon-β is selected from the group consisting of: human interferon-β 1b and human interferon-β 1b C17S.

12. The method of claim 10, wherein the recombinant Type 1 interferon protein is an interferon-α, and wherein the interferon-α is selected from the group consisting of: human interferon-α 2a and human interferon-α 2b.

13. The method of claim 4, wherein the expression construct comprises an inducible promoter.

14. The method of claim 13, wherein the expression construct comprises a lac promoter derivative and expression of the interferon is induced by isopropylthiogalactoside (IPTG).

15. The method of claim 14, wherein the host cell is grown
   at a temperature of about 25° C. to about 33° C.,
   at a pH of about 5.7 to about 6.5,
   and wherein the IPTG is added to a final concentration of about 0.08 mM to about 0.4 mM, when the $OD_{575}$ has reached about 80 to about 160.

16. The method of claim 15, wherein the host cell is grown
   at a temperature of about 32° C.,
   at a pH of about 5.7 to 6.25,
   and wherein the IPTG is added to a final concentration of about 0.2 mM, when the $OD_{575}$ has reached about 120 to about 160.

17. The method of claim 4 wherein the expression construct comprises a high activity ribosome binding site.

18. The method of claim 1, wherein the obtained soluble recombinant Type 1 interferon protein separated from other protein and cellular debris is present at a concentration of about 0.3 grams per liter to about 10 grams per liter.

19. The method of claim 1, wherein about 85% to about 100% of the separated soluble recombinant Type 1 interferon protein present is determined to be active.

20. The method of claim 19, wherein about 90% to about 100% of the separated soluble recombinant Type 1 interferon protein present is determined to be active.

21. The method of claim 20, wherein about 95% to about 100% of the separated soluble recombinant Type 1 interferon protein present is determined to be active.

22. The method of claim 1, wherein the host cell is a protease deletion strain.

23. The method of claim 22 wherein the host cell is a Ion hslUV protease deletion strain.

24. The method of claim 1, wherein the separated soluble recombinant Type 1 interferon protein is separated from the other protein and cellular debris by centrifugation, chromatography, or a combination thereof.

25. The method of claim 24, wherein the chromatography is size exclusion chromatography, anion exchange chromatography, cation exchange chromatography, hydrophobic interaction chromatography, affinity chromatography, or a combination thereof.

26. A method for extracting a recombinant Type I interferon protein, wherein the recombinant Type I interferon protein is present in an insoluble fraction, said insoluble fraction produced after lysis of a *Pseudomonas* or *E. coli* host cell expressing the recombinant Type I interferon protein, wherein the recombinant Type I interferon protein is expressed in the cytoplasm of the host cell, said method comprising:
   subjecting the insoluble fraction to non-denaturing extraction conditions, wherein the non-denaturing extraction conditions comprise a Zwitterionic detergent at about 0.5% to about 2%, to obtain soluble recombinant Type 1 interferon protein without the use of a renaturing or refolding step;
   separating the obtained soluble recombinant Type 1 interferon protein from other protein and cellular debris; and measuring the activity of the separated soluble recombinant Type 1 interferon protein, wherein about 80% to about 100% of the separated soluble recombinant Type 1 interferon protein is determined to be active.

27. The method of claim 26, wherein the separated soluble recombinant Type 1 interferon protein is separated from the other protein and cellular debris by centrifugation, chromatography, or a combination thereof.

28. The method of claim 27, wherein the chromatography is size exclusion chromatography, anion exchange chromatography, cation exchange chromatography, hydrophobic interaction chromatography, affinity chromatography, or a combination thereof.

* * * * *

SEQUENCE LISTING

```
<160> NUMBER OF SEQ ID NOS: 7

<210> SEQ ID NO 1
<211> LENGTH: 166
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 1

Met Ser Tyr Asn Leu Leu Gly Phe Leu Gln Arg Ser Ser Asn Phe Gln
1               5                   10                  15

Ser Gln Lys Leu Leu Trp Gln Leu Asn Gly Arg Leu Glu Tyr Cys Leu
            20                  25                  30

Lys Asp Arg Met Asn Phe Asp Ile Pro Glu Glu Ile Lys Gln Leu Gln
        35                  40                  45

Gln Phe Gln Lys Glu Asp Ala Ala Leu Thr Ile Tyr Glu Met Leu Gln
    50                  55                  60

Asn Ile Phe Ala Ile Phe Arg Gln Asp Ser Ser Ser Thr Gly Trp Asn
65                  70                  75                  80
```

Glu Thr Ile Val Glu Asn Leu Leu Ala Asn Val Tyr His Gln Ile Asn
                85                  90                  95

His Leu Lys Thr Val Leu Glu Glu Lys Leu Glu Lys Glu Asp Phe Thr
            100                 105                 110

Arg Gly Lys Leu Met Ser Ser Leu His Leu Lys Arg Tyr Tyr Gly Arg
        115                 120                 125

Ile Leu His Tyr Leu Lys Ala Lys Glu Tyr Ser His Cys Ala Trp Thr
    130                 135                 140

Ile Val Arg Val Glu Ile Leu Arg Asn Phe Tyr Phe Ile Asn Arg Leu
145                 150                 155                 160

Thr Gly Tyr Leu Arg Asn
                165

<210> SEQ ID NO 2
<211> LENGTH: 499
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 2
atgtcgtaca acctgttggg cttcctgcag cggtcctcca actttcaatc gcagaagctg      60
ctgtggcaat tgaatggtcg cctggaatac tgcctgaagg accgcatgaa cttcgacatc     120
cctgaagaga ttaagcaact ccagcagttc agaaagagg atgcagctct gacgatctat      180
gaaatgctgc agaacatctt cgcgatcttt cgccaggaca gcagcagcac cggttggaac     240
gaaaccattg tcgagaatct gctggccaac gtctatcacc agattaacca cctcaagact     300
gtgctggaag agaagttgga gaagaagat ttcacgcgtg gcaagttgat gagttcgctg      360
catttgaaac gctactatgg tcgtatcctg cattacctga aggccaaaga atacagccac     420
tgtgcgtgga ccatcgttcg cgtggagatc ctgcgcaact tctacttcat caatcggctc     480
accggttacc tccgcaact                                                 499

<210> SEQ ID NO 3
<211> LENGTH: 165
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 3

Ser Tyr Asn Leu Leu Gly Phe Leu Gln Arg Ser Ser Asn Phe Gln Ser
1               5                   10                  15

Gln Lys Leu Leu Trp Gln Leu Asn Gly Arg Leu Glu Tyr Cys Leu Lys
            20                  25                  30

Asp Arg Met Asn Phe Asp Ile Pro Glu Glu Ile Lys Gln Leu Gln Gln
        35                  40                  45

Phe Gln Lys Glu Asp Ala Ala Leu Thr Ile Tyr Glu Met Leu Gln Asn
    50                  55                  60

Ile Phe Ala Ile Phe Arg Gln Asp Ser Ser Ser Thr Gly Trp Asn Glu
65                  70                  75                  80

Thr Ile Val Glu Asn Leu Leu Ala Asn Val Tyr His Gln Ile Asn His
                85                  90                  95

Leu Lys Thr Val Leu Glu Glu Lys Leu Glu Lys Glu Asp Phe Thr Arg
            100                 105                 110

Gly Lys Leu Met Ser Ser Leu His Leu Lys Arg Tyr Tyr Gly Arg Ile
            115                 120                 125

Leu His Tyr Leu Lys Ala Lys Glu Tyr Ser His Cys Ala Trp Thr Ile
    130                 135                 140

Val Arg Val Glu Ile Leu Arg Asn Phe Tyr Phe Ile Asn Arg Leu Thr
145                 150                 155                 160

Gly Tyr Leu Arg Asn
                165

<210> SEQ ID NO 4
<211> LENGTH: 165
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 4

Cys Asp Leu Pro Gln Thr His Ser Leu Gly Ser Arg Arg Thr Leu Met
1               5                   10                  15

Leu Leu Ala Gln Met Arg Lys Ile Ser Leu Phe Ser Cys Leu Lys Asp
            20                  25                  30

Arg His Asp Phe Gly Phe Pro Gln Glu Glu Phe Gly Asn Gln Phe Gln
        35                  40                  45

Lys Ala Glu Thr Ile Pro Val Leu His Glu Met Ile Gln Gln Ile Phe
    50                  55                  60

Asn Leu Phe Ser Thr Lys Asp Ser Ser Ala Ala Trp Asp Glu Thr Leu
65                  70                  75                  80

Leu Asp Lys Phe Tyr Thr Glu Leu Tyr Gln Gln Leu Asn Asp Leu Glu
                85                  90                  95

Ala Cys Val Ile Gln Gly Val Gly Val Thr Glu Thr Pro Leu Met Lys
            100                 105                 110

Glu Asp Ser Ile Leu Ala Val Arg Lys Tyr Phe Gln Arg Ile Thr Leu
        115                 120                 125

Tyr Leu Lys Glu Lys Lys Tyr Ser Pro Cys Ala Trp Glu Val Val Arg
    130                 135                 140

Ala Glu Ile Met Arg Ser Phe Ser Leu Ser Thr Asn Leu Gln Glu Ser
145                 150                 155                 160

Leu Arg Ser Lys Glu
                165

<210> SEQ ID NO 5
<211> LENGTH: 495
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 5
tgtgacctgc ctcagactca ctccctcggt agccgccgga ccctgatgct gttggcgcag      60
atgcgtaaga tctccctgtt ctcgtgcctg aaagaccgcc atgatttcgg cttcccgcag     120
gaagaattcg ggaaccagtt tcagaaggct gaaaccatcc cagtgctgca cgagatgatc     180
cagcaaattt tcaacctgtt cagcaccaag gacagctcgg ccgcctggga cgaaacgttg     240
ttggacaaat tttacaccga gctgtaccaa caactgaacg atctggaagc atgcgttatt     300
caaggcgtgg gcgtcaccga aacgccgctg atgaaagaag atagcatcct ggccgtgcgt     360

```
aagtactttc agcgcatcac cctctacctg aaagagaaga agtattcgcc ctgcgcgtgg    420
gaggtcgtcc gcgccgagat catgcggtcc ttcagcctct ccaccaatct gcaggaaagt    480
ctccgctcga aagaa                                                      495
```

<210> SEQ ID NO 6
<211> LENGTH: 165
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 6

```
Cys Asp Leu Pro Gln Thr His Ser Leu Gly Ser Arg Arg Thr Leu Met
1               5                   10                  15

Leu Leu Ala Gln Met Arg Arg Ile Ser Leu Phe Ser Cys Leu Lys Asp
            20                  25                  30

Arg His Asp Phe Gly Phe Pro Gln Glu Glu Phe Gly Asn Gln Phe Gln
        35                  40                  45

Lys Ala Glu Thr Ile Pro Val Leu His Glu Met Ile Gln Gln Ile Phe
    50                  55                  60

Asn Leu Phe Ser Thr Lys Asp Ser Ser Ala Ala Trp Asp Glu Thr Leu
65                  70                  75                  80

Leu Asp Lys Phe Tyr Thr Glu Leu Tyr Gln Gln Leu Asn Asp Leu Glu
                85                  90                  95

Ala Cys Val Ile Gln Gly Val Gly Val Thr Glu Thr Pro Leu Met Lys
            100                 105                 110

Glu Asp Ser Ile Leu Ala Val Arg Lys Tyr Phe Gln Arg Ile Thr Leu
        115                 120                 125

Tyr Leu Lys Glu Lys Lys Tyr Ser Pro Cys Ala Trp Glu Val Val Arg
    130                 135                 140

Ala Glu Ile Met Arg Ser Phe Ser Leu Ser Thr Asn Leu Gln Glu Ser
145                 150                 155                 160

Leu Arg Ser Lys Glu
                165
```

<210> SEQ ID NO 7
<211> LENGTH: 495
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 7

```
tgtgacctgc ctcagactca ctccctcggt agccgccgga ccctgatgct gttggcgcag    60
atgcgtcgca tctccctgtt ctcgtgcctg aaagaccgcc atgatttcgg cttcccgcag   120
gaagaattcg gaaccagtt tcagaaggct gaaaccatcc cagtgctgca cgagatgatc    180
cagcaaattt tcaacctgtt cagcaccaag acagctcgg ccgcctggga cgaaacgttg    240
ttggacaaat tttacaccga gctgtaccaa caactgaacg atctggaagc atgcgttatt    300
caaggcgtgg gcgtcaccga aacgccgctg atgaagaag atagcatcct ggccgtgcgt    360
aagtactttc agcgcatcac cctctacctg aaagagaaga agtattcgcc ctgcgcgtgg    420
gaggtcgtcc gcgccgagat catgcggtcc ttcagcctct ccaccaatct gcaggaaagt    480
ctccgctcga aagaa                                                      495
```